(12) United States Patent
Scheidt et al.

(10) Patent No.: US 9,527,812 B2
(45) Date of Patent: Dec. 27, 2016

(54) N-HETEROCYCLIC CARBENE-CATALYZED SYNTHESIS OF 2-ARYL INDOLES

(71) Applicant: Northwestern University, Evanston, IL (US)

(72) Inventors: Karl A. Scheidt, Evanston, IL (US); Michael Todd Hovey, Jr., Evanston, IL (US); Christopher Check, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 14/701,814

(22) Filed: May 1, 2015

(65) Prior Publication Data

US 2015/0315143 A1     Nov. 5, 2015

Related U.S. Application Data

(60) Provisional application No. 61/987,207, filed on May 1, 2014.

(51) Int. Cl.
| | |
|---|---|
| C07D 209/08 | (2006.01) |
| C07D 409/04 | (2006.01) |
| C07D 401/04 | (2006.01) |
| C07D 209/10 | (2006.01) |
| C07D 209/14 | (2006.01) |
| C07D 209/12 | (2006.01) |
| C07D 209/26 | (2006.01) |

(52) U.S. Cl.
CPC ........... *C07D 209/08* (2013.01); *C07D 209/10* (2013.01); *C07D 209/12* (2013.01); *C07D 209/14* (2013.01); *C07D 209/26* (2013.01); *C07D 401/04* (2013.01); *C07D 409/04* (2013.01)

(58) Field of Classification Search
None
See application file for complete search history.

(56) References Cited

FOREIGN PATENT DOCUMENTS

WO       2005020921 A2    10/2005

OTHER PUBLICATIONS

Sun et al., 50 Angew Chem., Int. Ed., 1702-1706 (2011).*
Lv, H.; Jia, W.-Q.; Sun, L.-H.; Ye, S., "N-Heterocyclic Carbene Catalyzed [4+3] Annulation of Enals and o-Quinone Methides: Highly Enantioselective Synthesis of Benzo-e- Lactones", Angew. Chem. Int. Ed. 2013, 52, 8607-8610.
Vougioukalakis, G. C.; Grubbs, R. H., "Synthesis and Activity of Ruthenium Olefin Metathesis Catalysts Coordinated with Thiazol-2-ylidene Ligands", J. Am. Chem. Soc. 2008, 130, 2234-2245.
Piel, I.; Pawelczyk, M. D.; Hirano, K.; Fröhlich, R.; Glorius, F., "A Family of Thiazolium Salt Derived N-Heterocyclic Carbenes (NHCs) for Organocatalysis: Synthesis, Investigation and Application in Cross-Benzoin Condensation", Eur. J. Org. Chem. 2011, 5475-5484.
Cardinal-David, B.; Raup, D. E. A.; Scheidt, K. A., "Cooperative N-Heterocyclic Carbene/Lewis Acid Catalysis for Highly Stereoselective Annulation Reactions with Homoenolates", J. Am. Chem. Soc. 2010, 132, 5345-5347.
Padmanaban, M.; Biju, A. T.; Glorius, F., "N-Heterocyclic Carbene-Catalyzed Cross-Coupling of Aromatic Aldehydes with Activated Alkyl Halides", Org. Lett. 2011, 13, 98-101.
Inman, M.; Moody, C. J., "Indole synthesis—something old, something new", Chem. Sci. 2013, 4, 29-41.
Chen, C.-y.; Senanayake, C. H.; Bill, T. J.; Larsen, R. D.; Verhoeven, T. R.; Reider, P. J., "Improved Fischer Indole Reaction for the Preparation of N,N-Dimethyltryptamines: Synthesis of L-695,894, a Potent 5-HT1D Receptor Agonist", J. Org. Chem. 1994, 59, 3738-3741.
Haag, B. A.; Zhang, Z.-G.; Li, J.-S.; Knochel, P., "Fischer Indole Synthesis with Organozinc Reagents", Angew. Chem. Int. Ed. 2010, 49, 9513-9516.
Müler, S.; Webber, M. J.; List, B., "The Catalytic Asymmetric Fischer Indolization", J. Am. Chem. Soc. 2011, 133, 18534-18537.
Inman, M.; Carbone, A.; Moody, C. J., "Two-Step Route to Indoles and Analogues from Haloarenes: A Variation on the Fischer Indole Synthesis", J. Org. Chem. 2011, 77, 1217-1232.
Kuznetsov, A.; Makarov, A.; Rubtsov, A. E.; Butin, A. V.; Gevorgyan, V., "Brönsted Acid-Catalyzed One-Pot Synthesis of Indoles from o-Aminobenzyl Alcohols and Furans", J. Org. Chem. 2013, 78, 12144-12153.
Sridharan, V.; Perumal, S.; Avendalio, C.; Menéndez, J. C., "Microwave-Assisted, Solvent-Free Bischler Indole Synthesis", Synlett 2006, 91-95.
Vara, Y.; Aldaba, E; Arrieta, A.; Pizarro, J. L.; Arriortua, M. I.; Cossío, F. P., "Regiochemistry of the microwave-assisted reaction between aromatic amines and a-bromoketones to yield substituted 1H-indoles", Org. Biomol. Chem. 2008, 6, 1763-1772.
Wagaw, S.; Yang, B. H.; Buchwald, S. L., "A Palladium-Catalyzed Method for the Preparation of Indoles via the Fischer Indole Synthesis", J. Am. Chem. Soc. 1999, 121, 10251-10263.
Takeda, A.; Kamijo, S.; Yamamoto, Y., "Indole Synthesis via Palladium-Catalyzed Intramolecular Cyclization of Alkynes and Imines", J. Am. Chem. Soc. 2000, 122, 5662-5663.
Barluenga, J.; Trincado, M.; Rubio, E.; González, J. M., IPy2BF4-Promoted Intramolecular Addition of Masked and Unmasked Anilines to Alkynes: Direct Assembly of 3-Iodoindole Cores, Angew. Chem. Int. Ed. 2003, 42, 2406-2409.
Campos, K. R.; Woo, J. C. S.; Lee, S.; Tillyer, R. D., "A General Synthesis of Substituted Indoles from Cyclic Enol Ethers and Enol Lactones", Org. Lett. 2003, 6, 79-82.
Saito, A.; Kanno, A.; Hanzawa, Y., "Synthesis of 2,3-Disubstituted Indoles by a Rhodium-Catalyzed Aromatic Amino-Claisen Rearrangement of N-Propargyl Anilines", Angew. Chem. Int. Ed. 2007, 46, 3931-3933.
Trost, B. M.; McClory, A., "Rhodium-Catalyzed Cycloisomerization: Formation of Indoles, Benzofurans, and Enol Lactones", Angew. Chem. Int. Ed. 2007, 46, 2074-2077.
Cariou, K.; Ronan, B.; Mignani, S.; Fensterbank, L.; Malacria, M., "From PtCl2- and Acid-Catalyzed to Uncatalyzed Cycloisomerization of 2-Propargyl Anilines: Access to Functionalized Indoles", Angew. Chem. Int. Ed. 2007, 46, 1881-1884.

(Continued)

*Primary Examiner* — Timothy R Rozof
(74) *Attorney, Agent, or Firm* — Reinhart Boerner Van Deuren s.c.

(57) ABSTRACT

Transition metal-free catalytic methods for access to 2-arylindole compounds.

25 Claims, 1 Drawing Sheet

(56) References Cited

OTHER PUBLICATIONS

Barluenga, J.; Jiménez-Aquino, A.; Valdés, C.; Aznar, F., "The Azaallylic Anion as a Synthon for Pd-Catalyzed Synthesis of Heterocycles: Domino Two- and Three-Component Synthesis of Indoles", Angew. Chem. Int. Ed. 2007, 46, 1529-1532.
Stuart, D. R.; Bertrand-Laperle, M. g.; Burgess, K. M. N.; Fagnou, K., "Indole Synthesis via Rhodium Catalyzed Oxidative Coupling of Acetanilides and Internal Alkynes" J. Am. Chem. Soc. 2008, 130, 16474-16475.
Würtz, S.; Rakshit, S.; Neumann, J. J.; Dröge, T.; Glorius, F., Palladium-Catalyzed Oxidative Cyclization of N-Aryl Enamines: From Anilines to Indoles Angew. Chem. Int. Ed. 2008, 47, 7230-7233.
Shen, M.; Leslie, B. E.; Driver, T. G., "Dirhodium(II)-Catalyzed Intramolecular CH Amination of Aryl Azides", Angew. Chem. Int. Ed. 2008, 47, 5056-5059.
Shi, Z.; Zhang, C.; Li, S.; Pan, D.; Ding, S.; Cui, Y.; Jiao, N., "Indoles from Simple Anilines and Alkynes: Palladium-Catalyzed C-H Activation Using Dioxygen as the Oxidant", Angew. Chem. Int. Ed. 2009, 48, 4572-4576.
Bernini, R.; Fabrizi, G.; Sferrazza, A.; Cacchi, S., "Copper-Catalyzed C-C Bond Formation through C-H Functionalization: Synthesis of Multisubstituted Indoles from N-Aryl Enaminones", Angew. Chem. Int. Ed. 2009, 48, 8078-8081.
Stuart, D. R.; Alsabeh, P.; Kuhn, M.; Fagnou, K., "Rhodium(III)-Catalyzed Arene and Alkene C-H Bond Functionalization Leading to Indoles and Pyrroles", J. Am. Chem. Soc. 2010, 132, 18326-18339.
Stokes, B. J.; Liu, S.; Driver, T. G., "Rh2(II)-Catalyzed Nitro-Group Migration Reactions: Selective Synthesis of 3-Nitroindoles from (β-Nitro Styryl Azides)", J. Am. Chem. Soc. 2011, 133, 4702-4705.
Sun, K.; Liu, S.; Bec, P. M.; Driver, T. G., "Rhodium-Catalyzed Synthesis of 2,3-Disubstituted Indoles from B,B-Disubstituted Stryryl Azides", Angew. Chem. Int. Ed. 2011, 50, 1702-1706.
Cacchi, S.; Fabrizi, G.; Goggiamani, A.; Molinaro, C.; Verdiglione, R., Palladium-Catalyzed Synthesis of 2-(Aminomethyl)indoles from 3-(o-Trifluoroacetamidoaryl)-1-propargylic Alcohols and Amines J. Org. Chem. 2014, 401-407.
Larock, R. C.; Yum, E. K., "Synthesis of Indoles via Palladium-Catalyzed Heteroannulation of Internal Alkynes", J. Am. Chem. Soc. 1991, 113, 6689-6690.
Phipps, R. J.; Grimster, N. P.; Gaunt, M. J. J., "Cu(II)-Catalyzed Direct and Site-Selective Arylation of Indoles Under Mild Conditions", Am. Chem. Soc. 2008, 130, 8172-8174.
Raup, D. E. A.; Cardinal-David, B.; Holte, D.; Scheidt, K. A., "Cooperative Catalysis by Carbenes and Lewis Acids in a Highly Stereoselective Route to y-Lactams" Nat. Chem. 2010, 2, 766-771.
Stetter, H.; Landscheidt, "Addition of Aldehydes to Activated Double Bonds, XXI. Syntheses of 4,7-Dioxo-esters and 4,7-Dioxo-nitriles", A. Chem. Ber. 1979, 112, 2419-2422.
Stetter, H.; Basse, W.; Nienhaus, "Addition of Aldehydes to Activated Double Bonds, XXII. Addition of Aliphatic Aldehydes to α,β-Unsaturated Esters and Nitriles", J. Chem. Ber. 1980, 113, 690-698.
Mattson, A. E.; Bharadwaj, A. R.; Scheidt, K. A., "The Thiazolium-Catalyzed Sila-Stetter Reaction: Conjugate Addition of Acylsilanes to Unsaturated Esters and Ketones" J. Am. Chem. Soc. 2004, 126, 2314-2315.
Li, Y.; Shi, F.-Q.; He, Q.-L.; You, S.-L., "N-Heterocyclic Carbene-Catalyzed Cross-Coupling of Aldehydes with Arylsulfonyl Indoles", Org. Lett. 2009, 11, 3182-3185.
Toh, Q. Y.; McNally, A.; Vera, S.; Erdmann, N.; Gaunt, M. J., "Organocatalytic C—H Bond Arylation of Aldehydes to Bis-heteroaryl Ketones" J. Am. Chem. Soc. 2013, 135, 3772-3775.
Burgess, E. M.; McCullagh, L., N-Phenylbenzoazetine, J. Am. Chem. Soc. 1966, 88, 1580-1581.
Ikeda, M.; Matsugashita, S.; Tabusa, F.; Ishibashi, H.; Tamura, Y., "Photo-isomerisation of 1-Acetyl-2-cyano-1,2-dihydroquinolines to N-Acetylbenzoazetines", J. Chem. Soc., Chem. Commun. 1975, 575-576.
Lancaster, M.; Smith, D. J. H., "Preparation and Some Reactions of Benzazetidines", J. Chem. Soc., Chem. Commun. 1980, 471-472.
Wojciechowski, K., "Reactions of Aza-ortho-xylylenes Generated from 2,1-Benzisothiazoline 2,2-Dioxides", Tetrahedron 1993, 49, 7277-7286.
Ito, Y.; Miyata, S.; Nakatsuka, M.; Saegusa, T., "Synthesis of Nitrogen-Containing Polycycles on the Basis of a New Method of o-Quinone Methide Imine Generation", J. Am. Chem. Soc. 1981, 103, 5250-5251.
Bowen, R. D.; Davies, D. E.; Fishwick, C. W. G.; Glasbey, T. O.; Noyce, S. J.; Storr, R. C., "Generation and Reactions of Azaxylylenes", Tetrahedron Lett. 1982, 23, 4501-4504.
Foresti, E.; Spagnolo, P.; Zanirato, P., "Synthesis and Thermal Ring-cleavage Fragmentation of 2-Azido-1-methylindole and 2-Azidobenzo[b]furan", J. Chem. Soc., Perkin Trans. 1 1989, 1354-1356.
Lau, C. K.; Trimble, L.; Caille, A. S.; Wiebe, J. M., "Synthesis of Quinolines, Dihydro- and Tetrahydroquinolines via ortho-Quinone Methide Imine intermediate", Tetrahedron 1996, 52, 11705-11724.
Nishiyama, K.; Kubo, H.; Sato, T.; Higashiyama, K.; Ohmiya, S., "Facile IN SITU Preparation of o-Azaxylylene from N, O-Diethoxycarbonyl-o-Aminobenzyl Alcohol", Heterocycles 1998, 48, 1103-1106.
Steinhagen, H.; Corey, E., "A Convenient and Versatile Route to Hydroquinolines by Inter- and Intramolecular Aza-Diels-Alder Pathways", J. Angew. Chem. Int. Ed. 1999, 38, 1928-1931.
Avemaria, F.; Vanderheiden, S.; Bräse, S., "The aza-xylylene Diels-Alder approach for the synthesis of naturally occurring 2-alkyl tetrahydroquinolines", Tetrahedron 2003, 59, 6785-6796.
Yang, Q.-Q.; Xiao, C.; Lu, L.-Q.; An, J.; Tan, F.; Li, B.-J.; Xiao, W.-J., "Synthesis of Indoles through Highly Efficient Cascade Reactions of Sulfur Ylides and N-(ortho-Chloromethyl)aryl Amides", Angew. Chem. Int. Ed. 2012, 51, 9137-9140.
Yang, Q.-Q.; Wang, Q.; An, J.; Chen, J.-R.; Lu, L.-Q.; Xiao, W.-J., "Construction of Optically Active Indolines by Formal [4+1] Annulation of Sulfur Ylides and N-(ortho-Chloromethyl)aryl Amides", Chem.—Eur. J. 2013, 19, 8401-8404.
Mattson, A. E.; Scheidt, K. A., "Nucleophilic Acylation of o-Quinone Methides: An Umpolung Strategy for the Synthesis of r-Aryl Ketones and Benzofurans", J. Am. Chem. Soc. 2007, 129, 4508-4509.
Lv, H.; You, L.; Ye, S., "Enantioselective Synthesis of Dihydrocoumarins via N-Heterocyclic Carbene-Catalyzed Cycloaddition of Ketenes and o-Quinone Methides", Adv. Synth. Catal. 2009, 351, 2822-2826.
Izquierdo, J.; Orue, A.; Scheidt, K. A., "A Dual Lewis Base Activation Strategy for Enantioselective Carbene-Catalyzed Annulations", J. Am. Chem. Soc. 2013, 135, 10634-10637.
Lebrasseur, N. et al., "Recent Advances in the C2 and C3 Regioselective Direct Arylation of Indoles", Elsevier Inc., 2012; vol. 105, Chapter 4, pp. 309-351.
Resseirt, A. et al., "Einwirkung von Oxalester and Natriumäthylat auf Nitrotoluole. Synthese nitrirter Phenylbrenztraubensäuren", Chem. Ber. 1897, 30, 1030-1053.

\* cited by examiner

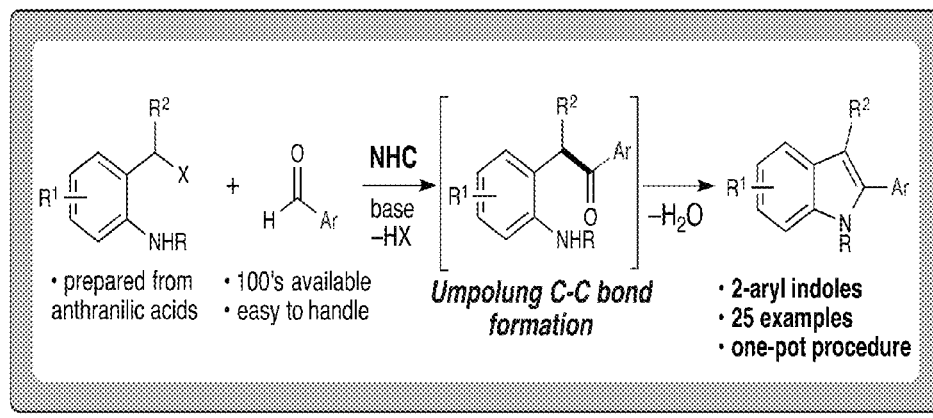

N-HETEROCYCLIC CARBENE-CATALYZED SYNTHESIS OF 2-ARYL INDOLES

This application claims priority to and the benefit of Application Ser. No. 61/987,207, filed May 1, 2014—the entirety of which is incorporated herein by reference.

This invention was made with government support under GM073072 awarded by the National Institutes of Health. The government has certain rights in the invention.

BACKGROUND OF THE INVENTION

The indole nucleus is the most common heterocycle found in nature. Many indole-containing compounds possess potent biological activity, which has earned this structural core the description of "privileged" in therapeutic discovery. Beginning with Möhlau and Fischer, the indole has captured the attention of the chemical community since the late 19th century. Historically, the most common method is the Fischer indole synthesis, but this reaction can be limited in scope due to the stability of the hydrazine component, preparation of aryl hydrazines, and strong acidic conditions. The Bischler-Möhlau synthesis of 2-aryl indoles usually requires high temperatures that can lead to low yields and regiochemistry problems.

In the development of new strategies to access this key heterocycle, modern chemical research has focused on transition metal-catalyzed approaches (Scheme 1a-d, prior art). For example, the Larock indole synthesis and Suzuki coupling strategies have enabled the synthesis of previously inaccessible indole scaffolds, with more recent work by Gaunt describing a copper-catalyzed arylation of indoles. While greatly expanding access to diverse indole structures, these methods use metal catalysts which can contaminate the desired products with difficult to remove toxic-metal impurities or require starting materials such as alkynes and prefunctionalized indoles.

SUMMARY OF THE INVENTION

In light of the foregoing, it is an object of the present invention to provide an indole synthesis overcoming various deficiencies and shortcomings of the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It can be an object of the present invention to provide an indole synthesis without use of a metal catalyst and without the need to remove metal impurities from the resulting indole product.

It can be another object of the present invention to provide a synthetic methodology for indole preparation via readily-available starting materials and moderate reaction conditions.

It can also be an object of the present invention, alone or in combination with one or more of the preceding objectives, to provide a facile indole synthesis which can be utilized en route to a range of therapeutic 2-aryl indole compounds.

Other objects, features, benefits and advantages of the present invention will be apparent from this summary and the following descriptions of certain embodiments, and will be readily apparent to those skilled in the art having knowledge of heterocycle synthesis. Such objects, features, benefits and advantages will be apparent from the above as taken into conjunction with the accompanying examples, data, figures and all reasonable inferences to be drawn therefrom, alone or with consideration of the references incorporated herein.

In part, the present invention can be directed to a method for preparation of 2-aryl indole compounds. Such a method can comprise providing a reaction medium comprising an o-aminobenzyl chloride compound, a base component and an N-heterocyclic carbene catalyst precursor compound; introducing 1,4-dioxane and an aryl aldehyde compound to such a reaction medium, to provide a benzylic ketone intermediate compound; and introducing an acid component to such a reaction medium, to promote intramolecular cyclization and dehydration, to provide a 2-aryl indole compound. In certain embodiments, without limitation, such a base component can be a non-nucleophilic carbonate. Regardless, such a catalyst precursor compound can be selected from azolium and thiazolium compounds. In certain such embodiments, such a catalyst precursor can be compound C, as illustrated below, and cesium carbonate can be employed as a base.

Irrespective of base or catalyst precursor identity, such a benzyl chloride compound can be of a formula

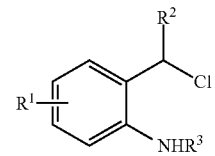

wherein $R^1$ can be selected from H, halo, cyano, alkyl, haloalkyl and alkoxy moieties; $R^2$ can be selected from H and alkyl moieties; and $R^3$ can be selected from H and amino protecting groups. Alternatively, a plurality of $R^1$ moieties can be present to provide corresponding multiple such moieties or combinations thereof.

Regardless of benzyl chloride identity, such an arylaldehyde compound can be of a formula ArC(O)H wherein Ar can be selected from aryl and heteroaryl moieties, such heteroatom(s) as can be selected from S and N to provide, without limitation, pyridyl and thiophenyl moieties and such an Ar moiety as can be optionally substituted with one or more halo, cyano, alkyl, haloalkyl, alkoxy, acetamido or acetamidoalkoxy groups and combinations thereof. With regard to certain embodiments, where Ar can be phenyl, such a benzaldehyde compound can be provided by hydrolysis of benzoin.

In part, the present invention can also be directed to an alternative method for 2-aryl indole synthesis. Such a method can comprise providing a reaction medium comprising an o-aminobenzyl chloride compound, an N-heterocyclic carbene catalyst precursor compound, a base component, 1,4-dioxane and an arylaldehyde compound of the sort described above or discussed elsewhere herein; and introducing thereto an acid component to promote intramolecular cyclization, dehydration and formation of a 2-aryl indole compound. As illustrated below, such a base component can be a non-nucleophilic carbonate; and a catalyst precursor compound can be independently selected from azolium and thiazolium compounds. In certain embodiments, catalyst precursor compound C, below, can be utilized in conjunction with cesium carbonate. Likewise, benzyl chloride and arylaldehyde compounds can be as discussed above and illustrated below. Regardless of starting material, base or catalyst identity, such a synthesis can be accomplished in a single reaction vessel without intermediate isolation or transfer of reaction medium.

In part, the present invention can also be directed to a method of using an N-heterocyclic carbene catalyst to prepare a 2-arylindole. Such a method can comprise providing a reaction medium comprising a thiazol-3-ium carbene catalyst precursor compound, a non-nucelophilic base component and an o-aminobenzyl chloride compound of the sort described above or discussed elsewhere herein, 1,4-dioxane and an arylaldehyde compound of the sort described above or discussed elsewhere herein; generating an acylanion component from such a carbene catalyst precursor compound in such a reaction medium; and introducing an acid component to such a reaction medium to promote intramolecular N—C bond formation and dehydration, to provide a 2-arylindole compound of the sort described above or discussed elsewhere herein. Such a method can be performed in a single reaction vessel absent intermediate isolation and/or absent transfer of reaction medium. In certain embodiments, catalyst precursor compound C, below, can be utilized in conjunction with cesium carbonate. Accordingly, as illustrated below, the methods of this invention can provide straight-forward, facile syntheses of compounds of particular theoretical or therapeutic interest.

Accordingly, the present invention can be directed to various 2-arylindole compounds heretofor unavailable. Without limitation, with reference to the preceding discussion, each of $R^1$ and $R^2$ can be H, $R^3$ can be selected from H and amino-protecting groups and Ar can be a 3,4-dibromophenyl moiety.

DETAILED DESCRIPTION OF THE DRAWINGS

FIG. 1 provides a schematic illustrative summary of a synthetic design utilized in conjunction with the present invention, to provide 2-arylindole compounds, in accordance with various non-limiting embodiments thereof.

DETAILED DESCRIPTION OF CERTAIN EMBODIMENTS

As illustrated by various non-limiting embodiments, the present invention provides an organocatalytic indole synthesis by harnessing Umpolung reactivity. In particular, N-heterocyclic carbenes (NHCs) can be employed as Lewis base catalysts to construct an array of carbocyclic, heterocyclic, and polycyclic compounds. As described below, a convergent synthesis of 2-aryl indoles is promoted by NHC catalysis under mild conditions.

A synthetic scheme was devised to provide for interception of a 2'-aminobenzylic ketone 1a (Scheme 1). The synthesis of an intermediate of this sort usually arises from acylation of a benzylic anion with subsequent reduction of the nitro moiety to promote C—N bond formation. As a departure from the prior art, it was surmised that this strategic ketone (1a) could be accessed in a conceptually distinct manner through an Umpulong disconnection from acyl-anion equivalent 1b and transient aza-ortho-quinone methide (Ao-QM) 1c reaction partners.

Scheme 1. 2-Aryl indole strategies.

Selected approaches to indoles: Metals or strong base required

Larock

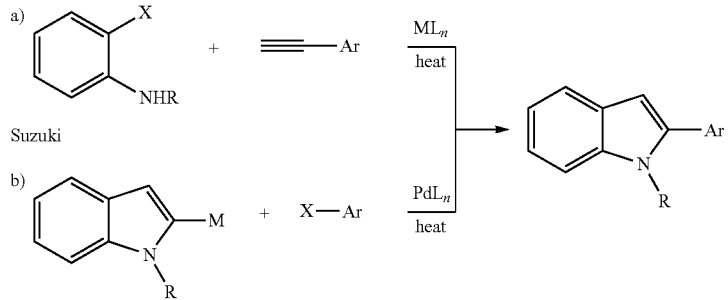

Suzuki

Gaunt

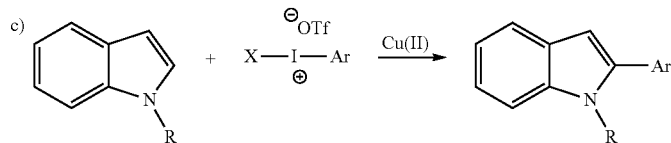

Reissert

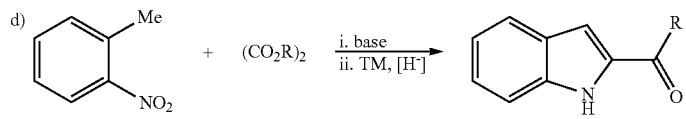

Umpolung approach: this work

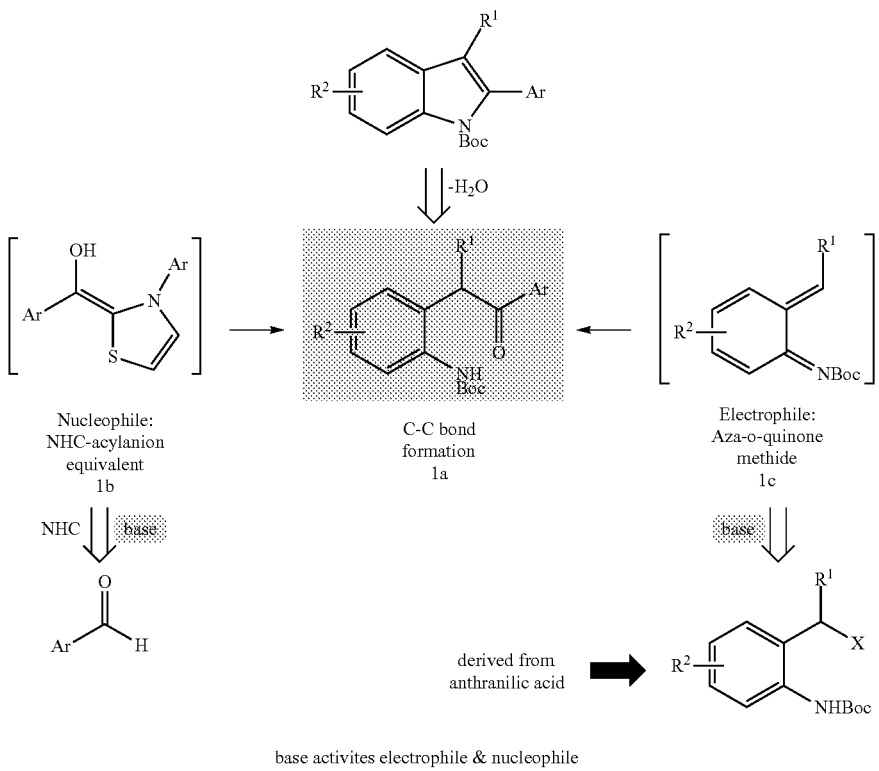

A base elimination strategy would allow for direct access from numerous commercially available, substituted anthranilic acids in 2-3 steps. Without limitation to any one theory or mode of operation, such an approach can be considered to provide concomitant generation of an Ao-QM and a NHC catalyst using a single Brønsted base species along with balancing the concentrations of each reactive intermediate during the course of the reaction (i.e., 1b and 1c). Initial experiments with benzyl chloride 2 and benzaldehyde in the presence of precatalysts A or B with DBU yielded the desired ketone 3 in moderate to low yield (Table 1, entry 1-2). Thorough investigation revealed the formation of unproductive adducts between nucleophilic bases (e.g., DBU, Et$_3$N) and chloride 2. In turn, an exhaustive screen of azolium precatalysts and solvents with non-nucleophilic cesium carbonate as base was undertaken. These experiments revealed that 30 mol % of azolium B in chloroform afforded the highest yield of ketone 3, 10 equiv. of aldehyde was required (entry 3).

TABLE 1

Optimization of Reaction Conditions.

| entry | NHC | base (equiv) | PhCHO (equiv) | solvent | yield 3[a] | yield 4[a] |
|---|---|---|---|---|---|---|
| 1 | A | DBU (1.5) | 1.5 | THF | 19[b] | — |
| 2 | B | DBU (1.5) | 1.5 | THF | 35[b] | — |
| 3[c] | B | Cs$_2$CO$_3$ (2.5) | 10 | CHCl$_3$ | 60 | — |
| 4 | C | Cs$_2$CO$_3$ (2.5) | 1.5 | THF | 82 | — |
| 5 | C | Cs$_2$CO$_3$ (2.5) | 1.0[d] | THF | 80 | — |
| 6 | C | Cs$_2$CO$_3$ (2.5) | 1.2 | THF | 86 | — |
| 7 | C | Cs$_2$CO$_3$ (1.2) | 1.2 | THF | 88 | — |
| 8[e] | C | Cs$_2$CO$_3$ (1.2) | 1.2 | 1,4-dioxane | — | 82 |
| 9[e,f] | C | Cs$_2$CO$_3$ (1.2) | 1.2 | 1,4-dioxane | — | 56 |
| 10[e,g] | C | Cs$_2$CO$_3$ (1.2) | 1.2 | 1,4-dioxane | — | 61 |
| 11 | C | K$_2$CO$_3$ (3.0) | 1.2 | 1,4-dioxane | 31[h] | — |

TABLE 1-continued

Optimization of Reaction Conditions.

| entry | NHC | base (equiv) | PhCHO (equiv) | solvent | yield 3[a] | yield 4[a] |
|-------|-----|--------------|---------------|---------|------------|------------|

A

B

C

D

[a] Isolated yield.
[b] Determined by 1H NMR spectroscopy (500 MHz) with 1,3,5-trimethoxybenzene as internal standard.
[c] 30 mol % azolium.
[d] Benzoin D used in place of benzaldehyde.
[e] After 36 h, 6.5 equiv MsOH was added.
[f] 10 mol % azolium.
[g] Reaction conducted at 50° C.
[h] Conversion after 36 h.

The promising yields obtained with azoliums A and B prompted exploration of several new N-aryl thiazoliums prepared with the 2,6-diethylphenyl moiety, which has been shown to increase catalyst performance. Thiazolium C afforded ketone 3 in 82% isolated yield in THF (entry 4). Notably, the replacement of benzaldehyde with benzoin D furnished the ketone in similar yield, providing evidence for the reversibility of the benzoin condensation under these conditions (entry 5). Importantly, the ability to cycle this undesired Umpolung product back into the desired reaction allows for less aldehyde substrate (i.e., 1.2 equiv) than typical intermolecular acyl anion reactions. Further improvement in yield was achieved by reducing the equivalents of benzaldehyde and cesium carbonate (entry 6-7).

With optimized conditions for the NHC/Ao-QM synthesis of ketone 3 developed, the in situ dehydration to prepare 2-aryl indole 4 was explored. The exposure of isolated ketone 3 to TFA in dichloromethane delivered the desired N-Boc indole in nearly quantitative yield (5 min, 96%). Unfortunately, the direct addition of TFA or other organic acids to the reaction mixture did not produce the desired results. Based on the results with TFA, it was thought that the Lewis basicity of the solvent could play a key role in the dehydration step. In order to streamline the indole synthesis to a single flask operation, without intermediate isolation or transfer of reaction medium, many ethereal solvents and organic acids were evaluated. With gratification, 1,4-dioxane mediated the NHC-catalyzed ketone synthesis as well as the acid-promoted dehydration. The addition of methanesulfonic acid promoted in situ dehydration of ketone 3 to the desired indole 4 (entry 8). Attempts to optimize further by reducing the precatalyst loading or by increasing reaction temperature reduced the overall yield (entry 9 and 10). The use of other bases, such as potassium carbonate, showed less than optimal conversion (entry 11).

With efficient single-flask conditions identified for the synthesis of 2-aryl indoles, the scope of this transformation was surveyed (Table 2). Aryl aldehydes with electron-withdrawing or donating groups in the para-position were tolerated, giving rise to the corresponding indoles in good to excellent yield (4a-4g). Furthermore, meta-substituted aryl aldehydes with electron-withdrawing and donating groups were accommodated under the reaction conditions, affording indoles 4h-4k in high yield.

TABLE 2

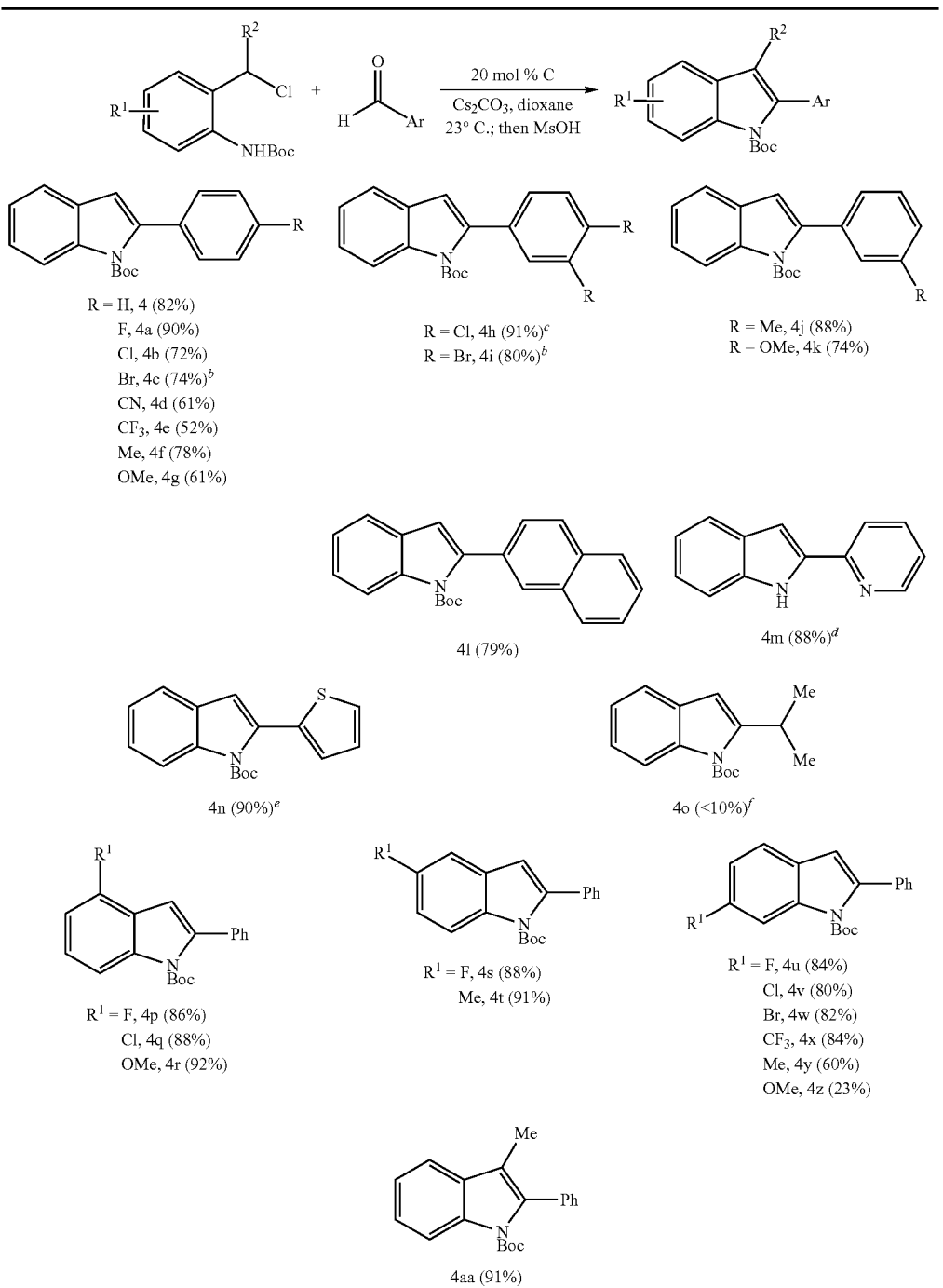

[a] See Examples, below, for details. Reactions conducted on 0.32 mmol scale. Isolated yield.
[b] Reaction conducted at 50° C.
[c] 2.2 equiv of aryl aldehyde.
[d] Deacylation occurred prior to dehydration over 12 h.
[e] Isolated as a 5:4 mixture of N-Boc/N-H indole.
[f] 20 mol % B.
[g] Starting material decomposes rapidly.

Indoles 4c and 4i were isolated in higher yield when the reaction was conducted at an elevated temperature (50° C.). Synthesis of indole 4i is noteworthy because it has never been prepared to date (N-Boc or N—H) and transition metal catalyzed strategies should prove difficult due to competing insertion reactions. The yield of indole 4h was significantly improved by increasing the amount of aryl aldehyde (2.2 equiv). At this time, and under the conditions employed, reactions with ortho-substituted aryl aldehydes provide recovery of unreacted starting materials or low conversion to the intermediate ketone. Either production of the nucleophilic Breslow intermediate (1b) may be slow and/or disfavored due to destabilizing interactions or once formed, the strain engendered may promote a conformational change placing the aryl ring orthogonal to the enol thiazolium system, thus sterically encumbering the nucleophilic acyl anion carbon (eq 1, below). Investigation of other representative aryl and heteroaryl-aldehydes produced corresponding indoles with 2-naphthyl (4l), pyridyl (4m), and thiophenyl (4n) C-2 substitutions. Aliphatic aldehydes (4o) showed only minimal activity with azolium B and no activity with C.

macologically active 2-aryl-indole was synthesized. Recent work by Exelixis showed that several 2-aryl-indoles are potent c-Kit kinase inhibitors (N—H and N-Boc indoles reported with $IC_{50}$ of 0.5-5.0 µmol, Scheme 2). In their approach, the synthesis of 7 relied on the use of a palladium catalyzed cross-coupling with a prefunctionalized indole boronic acid to construct the target in six steps overall. By contrast, present efforts began from commercially available aniline 5. A two-step amide formation and phenol alkylation

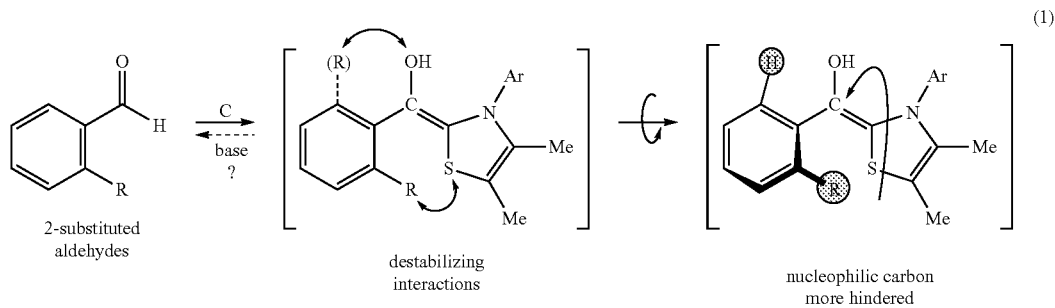

(1)

The tolerance of functionality and substitution on the amino-benzyl chloride 2, was also investigated. Both electron-withdrawing and electron-donating groups were tolerated at the C-4, C-5, C-6 positions affording indoles 4p-4z in moderate to high yield. The low yield observed for 4z was due to rapid decomposition of the starting material under the reactions conditions. Attempts to prepare indoles with substitution at C-7 proved unproductive, with only recovered starting material or decomposition at elevated reaction temperatures (50° C.) observed. Initial data suggests that ortho substitution of benzylic chlorides (2) impedes the deprotonation necessary for Ao-QM formation and approaches to circumvent this are currently being investigated. Lastly, substitution at the C-3 position (i.e., at the benzylic position of the benzylchloride starting material) gave access to indole 4aa in 91% isolated yield.

2-Aryl indoles have gained increased attention for their potential in therapeutic development. To demonstrate the practicality of this new indole synthesis, a reported pharmacologically active 2-aryl-indole was synthesized. yielded aldehyde 6 in 95% yield. Employing conditions of the sort described herein, a mixture of aldehyde 6 and aniline 2 gave heterocycle 7 in 83% yield. The route is unique in that only one chromatographic purification is required from benzyl chloride 2. In contrast, the reported proprietary synthesis required 6 steps and a Suzuki coupling involving 10 mol % Pd to furnish the C-2 arylated indole.

As demonstrated, a highly efficient, Umpolung synthesis of 2-aryl indoles using organocatalysis has been developed. The synthesis of a 2,6-diethylphenyl substituted thiazolium-derived NHC and modulation of the Lewis basicity of the solvent provided access to a wide range of indoles in high yield in a single flask operation. This represents the first indole synthesis facilitated by NHC catalysis. This new approach to these privileged heterocycles is operationally straightforward and provides for the incorporation of a wide range of aryl groups at the indole 2-position (See, e.g., FIG. 1) in good to excellent yield.

Scheme 2. Improved Synthesis of c-Kit Kinase Inhibitor 7.[a]

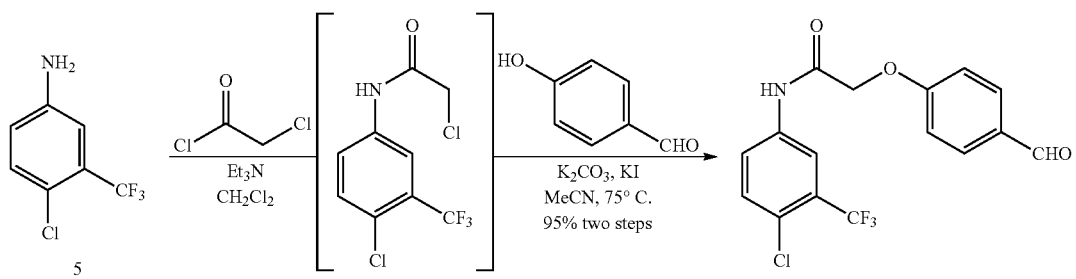

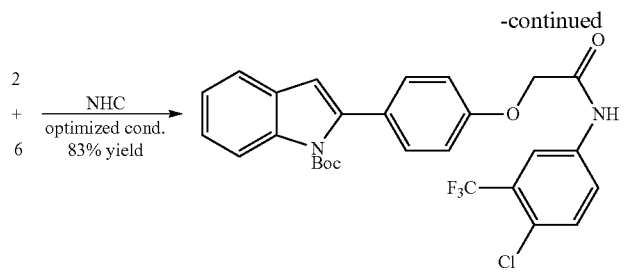

<sup>a</sup>See Examples, below, for details.

EXAMPLES OF THE INVENTION

The following non-limiting examples and data illustrate various aspects and features relating to the methods and/or compounds of the present invention, including the preparation of various 2-aryl indole compounds, as are available through the synthetic methodologies described herein. In comparison with the prior art, the present methods provide results and data which are surprising, unexpected and contrary thereto. While the utility of this invention is illustrated through the use of several aminobenzyl chloride and aryl aldehyde compounds and various substituents thereon, it will be understood by those skilled in the art that comparable results are obtainable with various other compounds and/or substituents, as are commensurate with the scope of this invention.

General Information.

All reactions were carried out under a nitrogen atmosphere in oven-dried glassware with magnetic stirring. 1,4-dioxane was dried over 4 Å molecular sieves and sparged with nitrogen gas for 1 hour before use. Reagents were purified prior to use unless otherwise stated following literature guidelines. (D. D. Perrin, W. L. Armarego, *Purification of Laboratory Chemicals;* 3rd Ed., Pergamon Press, Oxford, 1988.) Purification of reaction products was carried out by flash chromatography using EM Reagent or Silicycle silica gel 60 (230-400 mesh). Analytical thin layer chromatography was performed on EM Reagent 0.25 mm silica gel 60-F plates. Visualization was accomplished with UV light and ceric ammonium nitrate stain, anisaldehyde stain, or potassium permanganate stain followed by heating. Infrared spectra were recorded on a Bruker Tensor 37 FT-IR spectrometer. $^1$H-NMR spectra were recorded on a Bruker Avance 500 MHz w/ direct cryoprobe (500 MHz) spectrometer and are reported in ppm using solvent as an internal standard (CDCl$_3$ at 7.26 ppm). Data are reported as (ap=apparent, s=singlet, d=doublet, t=triplet, q=quartet, m=multiplet, b=broad; coupling constant(s) in Hz; integration). Proton-decoupled $^{13}$C-NMR spectra were recorded on a Bruker Avance 500 MHz w/ direct cryoprobe (126 MHz) spectrometer and are reported in ppm using solvent as an internal standard (CDCl3 at 77.0 ppm, d$_6$-DMSO at 39.5 ppm). Mass spectra data were obtained on a Waters Acquity Single Quadrupole ESI Spectrometer and Micromass Quadro II Spectrometer.

All aldehydes were purchased from commercial sources (Sigma Aldrich, Acros, Oakwood) and purified immediately before use. Aldehydes that were liquids at ambient temperature were distilled over calcium hydride under reduced pressure. All aldehydes that were solids at ambient temperature were dissolved in diethyl ether, washed with saturated sodium carbonate, followed by drying and concentration. Anthranilic acids were purchased from Oakwood and used without further purification.

Example 1

Procedure for Synthesis of 2,6-diethylphenyl N-aryl Thizaolium Precatalyst

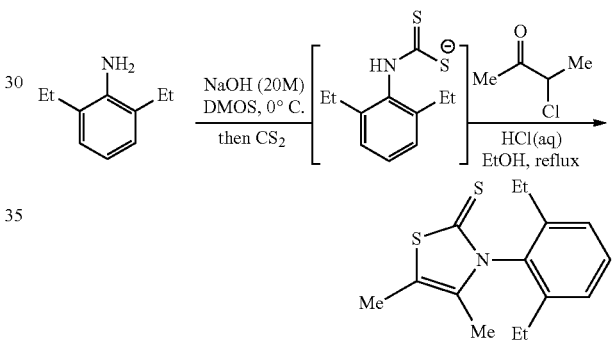

Example 1a 3-(2,6-diethylphenyl)-4,5-dimethylthiazole-2(3H)-thione. To a solution of 2,6-diethylaniline (5.82 mL, 35.3 mmol) dissolved in DMSO (17.7 mL) was added sodium hydroxide solution (20 M, 1.80 mL, 35.3 mmol) at ambient temperature with stirring. After 10 min, the flask was cooled in an ice-bath followed by drop-wise addition of carbon disulfide (2.128 ml, 35.3 mmol). The mixture was allowed to stir for 1 h at ambient temperature after which time the mixture was cooled in an ice-bath and 3-chlorobutan-2-one (3.57 mL, 35.3 mmol) was added with stirring. The ice-bath was removed and stirred at ambient temperature overnight. Water (DI, 35 mL) was added and the mixture was stirred at 0° C. for 10 min. Then the supernatant solution was decanted three times. The resulting slurry was dissolved in ethanol (40 ml), added concentrated hydrogen chloride (2.0 mL) and refluxed for 1 h followed by cooling and placement in a freezer at −30° C. overnight to promote precipitation. The precipitate was filtered off and washed with n-pentane (25 mL) to afford thione SI-1 as a light orange solid (5.37 g, 19.4 mmol, 55%). No further purification was required. Analytical data for SI-1: $^1$H NMR (500 MHz, CDCl$_3$) δ 7.42 (t, J=7.7 Hz, 1H), 7.27 (d, J=7.4 Hz, 2H), 2.42 (dq, J=15.2, 7.6 Hz, 2H), 2.29 (dq, J=15.2, 7.6 Hz, 2H), 2.22 (d, J=1.2 Hz, 3H), 1.73 (d, J=1.3 Hz, 3H), 1.22 (t, J=7.6 Hz, 6H). $^{13}$C NMR (CDCl$_3$, 126 MHz) δ 186.6, 140.9, 135.4, 134.3, 129.8, 126.4, 118.2, 23.6, 13.5, 12.9, 11.9; IR (film) cm$^{-1}$ 3012, 2670, 2929, 2873, 1620, 1461, 1335, 1304, 1232, 1049, 805; Mp: 111-112° C.; LRMS (ESI): Mass calcd for [M+H]$^+$ C$_{15}$H$_{20}$NS$_2$: 278.1; found 278.1.

Example 1b

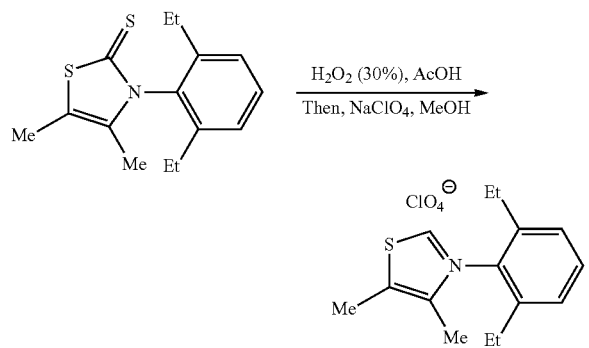

3-(2,6-diethylphenyl)-4,5-dimethylthiazol-3-ium perchlorate (C). To a solution of the thione of example 1a (3.0 g, 10.81 mmol) dissolved in glacial acetic acid (43.3 mL) was added hydrogen peroxide (30% by wt in H$_2$O, 3.56 mL, 35.7 mmol) drop-wise at 0° C. followed by stirring at 0° C. for 1 h. After the solvent and other volatiles were removed in vacuo, the residue was dissolved in methanol (10 mL) followed by addition of sodium perchlorate (5.41 g, 44.2 mmol) in a solution of methanol/water (2:1, 40 mL) at 0° C. After stirring for 30 min, water (15 mL) was added and the mixture was extracted with dichloromethane (3×25 mL). The combined organic layers were dried with anhydrous sodium sulfate and the solvent was removed in vacuo. The impure residue was recrystallized from a dichloromethane/ether/methanol mixture (5:5:1, 20 mL) to afford the desired thiazolium C as a fine tan powder (3.34 g, 9.66 mmol, 89%). Analytical data for C: $^1$H NMR (500 MHz, CDCl$_3$) δ 9.76 (s, 1H), 7.55 (t, J=7.8 Hz, 1H), 7.33 (d, J=7.7 Hz, 2H), 2.69 (s, 3H), 2.18 (ddt, J=19.8, 15.3, 7.7 Hz, 4H), 2.11 (s, 3H), 1.15 (t, J=7.5 Hz, 6H). $^{13}$C NMR (CDCl$_3$, 126 MHz) δ 156.5, 142.1, 139.5, 135.2, 133.9, 132.1, 127.5, 23.6, 14.0, 12.9, 11.5; IR (film) cm$^{-1}$ 3093, 2973, 2938, 2879, 2359, 2008, 1583, 1461, 1247, 1094, 818, 779, 623; Mp: 158-159° C.; LRMS (ESI): Mass calcd for [M]$^+$ C$_{15}$H$_{21}$NS: 246.1; found 246.1.

Example 2

General Procedure for Synthesis of N-Boc-Amino Benzyl Chlorides

Preparation of o-Amino-benzyl Alcohols

Example 2a

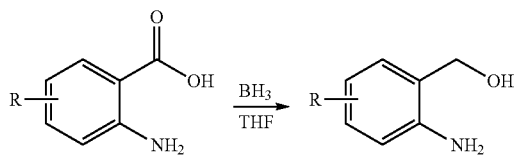

Into a 100 mL round-bottom flask equipped with a magnetic stirbar was added anthranilic acid derivative (1.0 equiv) and tetrahydrofuran (1.0 M). The mixture was then cooled to 0° C. with an ice bath and to it was added a 1.0 M solution of borane in tetrohydrofuran (2.0-3.0 equiv) with venting. After addition, the reaction vessel was put under a nitrogen atmosphere and heated to 30-35° C. for 12-36 hours. Upon consumption of the starting material (as observed by $^1$H-NMR spectroscopy) the flask was placed into an ice-bath, opened to the atmosphere, and with vigorous stirring, tetrahydrofuran and deionized water (1:1, 40 mL) were added drop-wise until gas evolution was no longer observed. The aqueous phase was then saturated with solid anhydrous potassium carbonate (WARNING: vigorous gas evolution) and the ice bath removed. After warming to ambient temperature the mixture was transferred to a separatory funnel containing diethyl ether (50 mL) and deionized water (10 mL). The organic and aqueous layers were separated and the aqueous portion was extracted with diethyl ether (3×25 mL). The organic portions were combined, washed with brine, dried over anhydrous magnesium sulfate, and filtered. The solvent was removed in vacuo, affording the ortho-amino-benzyl alcohols, which were used in the next step without further purification.

Example 2B

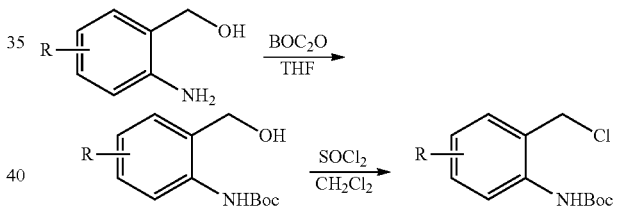

Method A:

Into a round bottom flask equipped with a magnetic stirbar was added o-amino-benzyl alcohol (1.0 equiv) followed by THF (0.3 M) and di-tert-butyl dicarbonate (1.05 equiv). The reaction was stirred under nitrogen for 12-36 h. Upon consumption of the starting material (TLC), the reaction solvent was removed in vacuo and the residue was purified by flash chromatography (15%-35% EtOAc/hexanes) to afford the corresponding N-Boc-amino-benzyl alcohol. The material was used in the next step without further characterization. Into a round bottom flask equipped with a magnetic stirbar was added N-Boc-o-amino-benzyl alcohol (1.0 equiv) followed by dichloromethane (0.2 M). The flask was placed in an ice-bath and cooled to 0° C., at which time thionyl chloride (1.05 equiv) was added drop-wise with venting under a stream of nitrogen. The flask was removed from the ice-bath and allowed to stir at ambient temperature with venting for 0.5-3 h. Once complete (TLC), the reaction solvent was removed in vacuo and the residue was purified by flash chromatography (15%-35% EtOAc/hexanes) to afford the corresponding N-Boc-amino-benzyl chloride.

Example 2C

Method B:

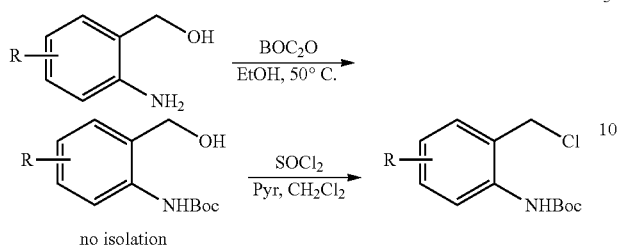

no isolation

Into a round bottom flask equipped with a magnetic stirbar was added o-amino-benzyl alcohol (1.0 equiv) followed by ethanol (0.5 M) and di-tert-butyl dicarbonate (1.1 equiv). The reaction was stirred under nitrogen for 24-48 h at 45-50° C. Upon consumption of the starting material ($^1$H-NMR spectroscopy) the reaction solvent was removed in vacuo, followed by repeated dilution with dichloromethane (3×30 mL) and removal of solvent in vacuo to afford analytically pure N-Boc-o-amino benzyl alcohol. To the same round bottom flask equipped with a magnetic stirbar was added dichloromethane (0.2 M) and placed into an ice-bath. For sensitive substrates pyridine (1.1 equiv) was added followed by dropwise addition of thionyl chloride (1.05 equiv). The ice-bath was removed and the mixture was stirred at ambient temperature under nitrogen for 1-3 h until complete (TLC). If no pyridine was added, the solvent was removed in vacuo and the residue was immediately purified by column chromatography (20%-30% EtOAc/hexanes) to afford the corresponding N-Boc-amino-benzyl chloride. If pyridine was used the reaction was quenched by addition of dilute aqueous hydrogen chloride (1:1, 1.0 M HCl (aq) and DI water, 20 mL) and transferred to a separatory funnel. The organic portion was removed and the aqueous portion was extracted with dichloromethane (3×20 mL). The organic portions were combined, dried over anhydrous sodium sulfate, and the solvent removed in vacuo to yield the N-Boc-amino-benzyl chloride. Many were used without further purification, but if necessary, column chromatography (20%-30% EtOAc/hexanes) afforded analytically pure N-Boc-amino-benzyl chloride.

Example 3

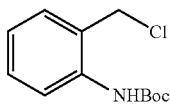 [SMILES: CC(C)(C)OC(=O)Nc1ccccc1CCl]

tert-butyl (2-(chloromethyl)phenyl)carbamate (2): Prepared according to Method B starting from (2-aminophenyl) methanol. The unpurified residue did not require further purification thus affording benzyl chloride 2 as a pale off-white solid (5.5 g, 75% over 2 steps, avg of >5 preparations). Analytical data for 2: $^1$H NMR (500 MHz, CDCl$_3$) δ 7.85 (d, J=7.8 Hz, 1H), 7.39-7.32 (m, 1H), 7.27 (dd, J=7.6, 1.3 Hz, 1H), 7.07 (td, J=7.5, 0.9 Hz, 1H), 6.76 (s, 1H), 4.62 (s, 2H), 1.54 (s, 9H). $^{13}$C NMR (CDCl$_3$, 126 MHz) δ 152.9, 137.0, 130.0, 129.9, 126.9, 123.9, 122.6, 80.8, 44.1, 28.3; IR (film) cm$^{-1}$ 3419, 3067, 2979, 2932, 1732, 1591, 1523, 1454, 1368, 1302, 1325, 1158, 763, 668; Mp: 81-82° C.; LRMS (EI): Mass calcd for [M]$^+$ C$_{12}$H$_{16}$ClNO$_2$: 241.1; found 241.1.

Example 4

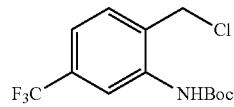

tert-butyl (2-(chloromethyl)-5-(trifluoromethyl)phenyl) carbamate (SI-2): Prepared according to Method A starting from 2-amino-4-(trifluoromethyl)benzoic acid. The unpurified residue was purified by column chromatography (20%-30% EtOAc/hexanes) to afford benzyl chloride SI-2 as a pale yellow solid (0.330 g, 61% over 3 steps). Analytical data for SI-2: $^1$H NMR (500 MHz, CDCl$_3$) δ 8.25 (br. s, 1H), 7.39 (d, J=7.9 Hz, 1H), 7.31 (d, J=8.0 Hz, 1H), 6.87 (s, 1H), 4.62 (s, 2H), 1.55 (s, 9H). $^{13}$C NMR (CDCl$_3$, 126 MHz) δ 152.4, 137.7, 132.1 (q, J$_{C-F}$=32.6 Hz), 130.3, 139.4, 123.6 (q, J$_{C-F}$=272.5 Hz), 120.1 (d, J$_{C-F}$=3.8 Hz), 118.7, 81.6, 43.0, 28.2; IR (film) cm$^{-1}$ 3420, 3257, 3012, 2986, 2932, 2365, 1680, 1333, 1161, 1126, 871; Mp: 94-95° C.; LRMS (EI): Mass calcd for [M]$^+$ C$_{13}$H$_{15}$ClF$_3$NO$_2$: 309.1; found 309.1.

Example 5

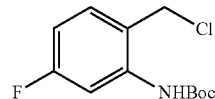

tert-butyl (2-(chloromethyl)-5-fluorophenyl)carbamate (SI-3): Prepared according to Method B (with pyridine) starting from 2-amino-4-fluorobenzoic acid (1.20 g, 7.74 mmol). The unpurified orange solid did not require further purification (1.30 g, 68% over three steps). Analytical data for SI-3: $^1$H NMR (500 MHz, CDCl$_3$) δ 7.80-7.74 (br. d, 1H), 7.21 (dd, J=8.5, 6.2 Hz, 1H), 6.87 (s, 1H), 6.73 (td, J=8.1, 2.6 Hz, 1H), 4.58 (s, 2H), 1.54 (s, 9H). $^{13}$C NMR (CDCl$_3$, 126 MHz) δ 163.6 (d, J$_{C-F}$=247.1 Hz), 152.5, 139.0 (d, J$_{C-F}$=11.8 Hz), 131.3 (d, J$_{C-F}$=9.9 Hz), 121.5, 110.2 (d, J$_{C-F}$=22.0 Hz), 109.1 (d, J$_{C-F}$=27.2 Hz), 81.5, 43.7, 28.3; IR (film) cm$^{-1}$ 3420, 3009, 2980, 2932, 2365, 1734, 1524, 1234, 1158, 983; Mp: 44-46° C.; LRMS (EI): Mass calcd for [M]$^+$ C$_{12}$H$_{15}$ClFNO$_2$: 259.1; found 259.1.

Example 6

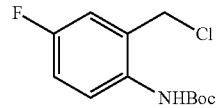

tert-butyl (2-(chloromethyl)-4-fluorophenyl)carbamate (SI-4): Prepared according to Method B (with pyridine) starting from 2-amino-5-fluorobenzoic acid (1.20 g, 7.74 mmol). The unpurified white solid did not require further purification (1.65 g, 82% over three steps). Analytical data SI-4: ¹H NMR (500 MHz, CDCl₃) δ 7.73 (s, 1H), 7.13-6.94 (m, 2H), 6.58 (s, 1H), 4.56 (s, 2H), 1.53 (s, 9H); ¹³C NMR (CDCl₃, 126 MHz) δ 159.0 (d, $J_{C-F}$=244.4 Hz), 153.3, 132.8 (d, $J_{C-F}$=2.9 Hz), 130.2, 129.9, 125.3, 116.5 (d, $J_{C-F}$=22.7 Hz), 81.1, 43.2, 28.3; IR (film) cm⁻¹ 3342, 2974, 2932, 2387, 1690, 1521, 1165; Mp: 96-98° C.; LRMS (EI): Mass calcd for [M]⁺ $C_{12}H_{15}ClFNO_2$: 259.1; found 259.1.

Example 7

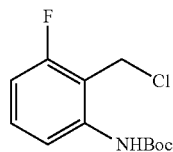 [SMILES: CC(C)(C)OC(=O)Nc1cccc(F)c1CCl]

tert-butyl (2-(chloromethyl)-3-fluorophenyl)carbamate (SI-5): Prepared according to Method A starting from 2-amino-6-fluorobenzoic acid. The residue was purified by column chromatography (20%-30% EtOAc/hexanes) to yield benzyl chloride SI-5 as a tan solid (0.22 g, 63% over three steps). Analytical data SI-5: ¹H NMR (500 MHz, CDCl₃) δ 7.70 (d, J=8.3 Hz, 1H), 7.30 (td, J=8.3, 6.4 Hz, 1H), 6.82 (d, J=8.8 Hz, 1H), 6.76 (s, 1H), 4.70 (s, 2H), 1.54 (s, 9H); ¹³C NMR (CDCl₃, 126 MHz) δ 163.6 (d, $J_{C-F}$=247.1 Hz), 152.5, 139.0 (d, $J_{C-F}$=11.8 Hz), 131.3 (d, $J_{C-F}$=9.9 Hz), 121.5, 110.2 (d, $J_{C-F}$=22.0 Hz), 109.1 (d, $J_{C-F}$=27.2 Hz), 81.5, 43.7, 28.3; IR (film) cm⁻¹ 3343, 2982, 2928, 2384, 1687, 1445, 1249, 1158; Mp: 88-89° C.; LRMS (EI): Mass calcd for [M]⁺ $C_{12}H_{15}ClFNO_2$: 259.1; found 259.1.

Example 8

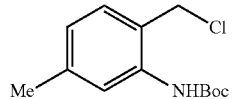

tert-butyl (2-(chloromethyl)-5-methylphenyl)carbamate (SI-6): Prepared according to Method A starting from 2-amino-4-methylbenzoic acid. The residue was purified by column chromatography (20%-30% EtOAc/hexanes) to yield benzyl chloride SI-6 as a white solid (0.102 g, 54% over three steps). Analytical data SI-6: ¹H NMR (500 MHz, CDCl₃) δ 7.71 (s, 1H), 7.15 (d, J=7.7 Hz, 1H), 6.92-6.83 (m, 1H), 6.74 (s, 1H), 4.60 (s, 2H), 2.35 (s, 3H), 1.54 (s, 9H); ¹³C NMR (CDCl₃, 126 MHz) δ 153.0, 140.4, 136.9, 129.9, 124.7, 123.9, 123.0, 80.8, 44.3, 28.4, 21.5; IR (film) cm⁻¹ 3413, 3015, 2977, 2929, 1731, 1585, 1527, 1237, 1158; Mp: 68-69° C.; LRMS (EI): Mass calcd for major fragment [M-tBu—Cl]⁺ $C_9H_9NO_2$: 163.1; found 162.9.

Example 9

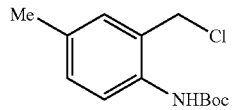

tert-butyl (2-(chloromethyl)-4-methylphenyl)carbamate (SI-7): Prepared according to Method B starting from 2-amino-5-methylbenzoic acid. The unpurified light orange solid did not require further purification (1.65 g, 95% over three steps). Analytical data SI-7: ¹H NMR (500 MHz, CDCl₃) δ 7.67 (d, J=6.6 Hz, 1H), 7.15 (dd, J=8.3, 1.5 Hz, 1H), 7.09 (d, J=1.4 Hz, 1H), 6.64 (s, 1H), 4.58 (s, 2H), 2.30 (s, 3H), 1.53 (s, 9H). ¹³C NMR (CDCl₃, 126 MHz) δ 153.1, 134.3, 133.8, 130.5, 130.4, 127.3, 123.1, 80.6, 44.1, 28.3, 20.6; IR (film) cm⁻¹ 3421, 3041, 2978, 2929, 1728, 1594, 1520, 1369, 1244, 1161, 1051, 861; Mp: 71-72° C.; LRMS (EI): Mass calcd for [M]⁺ $C_{13}H_{18}ClNO_2$: 255.1; found 255.1.

Example 10

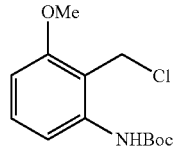 [SMILES: COc1cccc(NC(=O)OC(C)(C)C)c1CCl]

tert-butyl (2-(chloromethyl)-3-methoxyphenyl)carbamate (SI-8): Prepared according to Method B (with pyridine) starting from 2-amino-6-methoxybenzoic acid. The unpurified residue was purified by column chromatography (20%-30% EtOAc/hexanes) to yield benzyl chloride SI-8 as a brown oil (0.200 g, 59% over three steps). Analytical data SI-8: ¹H NMR (500 MHz, CDCl₃) δ 7.48 (d, J=8.4 Hz, 1H), 7.28 (t, J=8.4 Hz, 1H), 6.72 (s, 1H), 6.65 (d, J=8.3 Hz, 1H), 4.77 (s, 2H), 3.86 (s, 3H), 1.53 (s, 9H); ¹³C NMR (CDCl₃, 126 MHz) δ 157.4, 153.0, 138.4, 130.2, 115.7, 114.8, 106.2, 80.9, 55.9, 37.1, 28.3; IR (film) cm⁻¹ 3051, 2978, 2924, 2357, 1728, 1453, 1326, 1161, 1031, 809; LRMS (EI): Mass calcd for major fragment [M-tBu—Cl]⁺ $C_9H_9NO_3$: 179.1; found 179.1.

Example 11

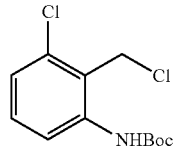 [SMILES: CC(C)(C)OC(=O)Nc1cccc(Cl)c1CCl]

tert-butyl (3-chloro-2-(chloromethyl)phenyl)carbamate (SI-9): Prepared according to Method B starting from 2-amino-6-chlorobenzoic acid. The unpurified residue was purified by column chromatography (20%-30% EtOAc/hexanes) to yield benzyl chloride SI-9 as a light yellow solid (0.102 g, 50% over three steps). Analytical data SI-9: ¹H NMR (500 MHz, CDCl₃) δ 7.78 (d, J=8.3 Hz, 1H), 7.27 (t, J=8.2 Hz, 1H), 7.16 (dd, J=8.0, 1.3 Hz, 1H), 6.74 (s, 1H), 4.82 (s, 2H), 1.54 (s, 9H). ¹³C NMR (CDCl₃, 126 MHz) δ 152.7, 138.7, 134.4, 130.1, 125.3, 125.0, 121.4, 81.3, 39.8, 28.20; IR (film) cm⁻¹ 3347, 3031, 2988, 2936, 1693, 1575, 1432, 1251, 941; Mp: 104-105° C.; LRMS (EI): Mass calcd for [M]⁺ $C_{12}H_{15}Cl_2NO_2$: 275.1; found 275.1.

Example 12

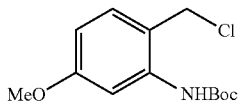

tert-butyl (2-(chloromethyl)-5-methoxyphenyl)carbamate (SI-10): Prepared according to Method B starting from 2-amino-4-methoxybenzoic acid (1.1 g, 7.2 mmol). The unpurified residue was purified by column chromatography (20%-30% EtOAc/hexanes) to yield benzyl chloride SI-10 as a light orange oil (0.61 gx, 31% over three steps). Analytical data SI-10: $^1$H NMR (500 MHz, CDCl$_3$) δ 7.60-7.49 (m, 1H), 7.14 (d, J=8.4 Hz, 1H), 6.82 (s, 1H), 6.58 (dd, J=8.4, 2.6 Hz, 1H), 4.59 (s, 2H), 3.80 (s, 3H), 1.54 (s, 9H). $^{13}$C NMR (CDCl$_3$, 126 MHz) δ 160.9, 152.6, 138.4, 130.9, 118.2, 109.6, 106.9, 80.8, 55.3, 44.3, 28.2; IR (film) cm$^{-1}$ 3419, 3067, 2979, 2932, 1732, 1591, 1523, 1235, 1158; LRMS (EI): Mass calcd for [M—CH$_2$—Cl]$^+$ C$_{12}$H$_{17}$NO$_3$: 223.1; found 223.1.

Example 13

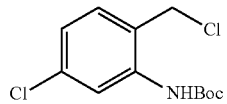 [SMILES: CC(C)(C)OC(=O)Nc1cc(Cl)ccc1CCl]

tert-butyl (5-chloro-2-(chloromethyl)phenyl)carbamate (SI-11): Prepared according to Method B starting from 2-amino-4-chlorobenzoic acid (1.2 g, 6.99 mmol). The unpurified light yellow solid did not require further purification (1.50 g, 78% over three steps). Analytical data SI-11: $^1$H NMR (500 MHz, CDCl$_3$) δ 8.01 (s, 1H), 7.18 (d, J=8.2 Hz, 1H), 7.03 (dd, J=8.2, 2.1 Hz, 1H), 6.80 (s, 1H), 4.57 (s, 2H), 1.54 (s, 9H). $^{13}$C NMR (CDCl$_3$, 126 MHz) δ 152.4, 138.2, 135.8, 130.8, 124.4, 123.6, 121.9, 81.4, 43.4, 28.2; IR (film) cm$^{-1}$ 3417, 3006, 2980, 2965, 2362, 1731, 1585, 1515, 1234, 1155, 865; Mp: 86-88° C.; LRMS (EI): Mass calcd for [M]$^+$ C$_{12}$H$_{15}$Cl$_2$NO$_2$3: 275.1; found 275.1.

Example 14

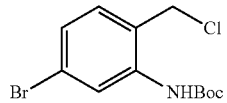

tert-butyl (5-bromo-2-(chloromethyl)phenyl)carbamate (SI-12): Prepared according to Method B starting from 2-amino-4-bromobenzoic acid (1.2 g, 5.55 mmol). The unpurified light orange solid did not require further purification (1.4 g, 73% over three steps). Analytical data SI-12: $^1$H NMR (500 MHz, CDCl$_3$) δ 8.15 (s, 1H), 7.18 (dd, J=8.1, 2.0 Hz, 1H), 7.12 (d, J=8.1 Hz, 1H), 6.79 (br. s, 1H), 4.55 (s, 2H), 1.54 (s, 9H). $^{13}$C NMR (CDCl$_3$, 126 MHz) δ 152.4, 138.3, 131.0, 126.6, 124.9, 124.8, 123.8, 81.4, 43.4, 28.2; IR (film) cm$^{-1}$ 3413, 3006, 2980, 2932, 2362, 1732, 1511, 1155, 858; Mp: 89-91° C.; LRMS (EI): Mass calcd for [M]$^+$ C$_{12}$H$_{15}$BrClNO$_2$: 319.0; found 319.0.

Example 15

Synthesis of tert-butyl (2-(1-chloroethyl)phenyl)carbamate SI-13

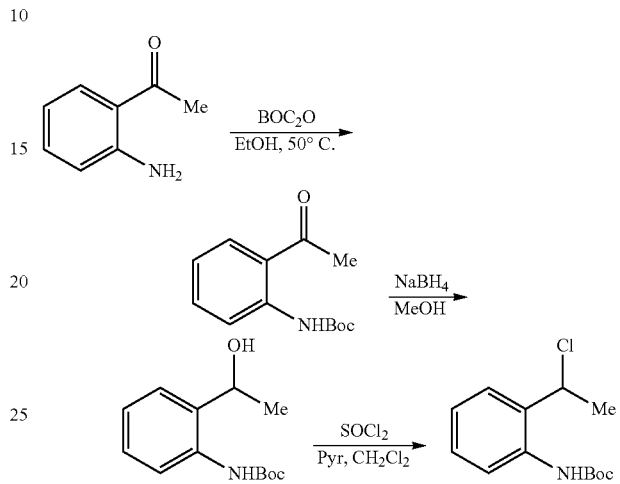

To a solution of 1-(2-aminophenyl)ethanone (1.081 mL, 8.88 mmol, 1.0 equiv) in ethanol (18 mL, 0.5 M) was added di-tert-butyl dicarbonate (7.75 g, 35.5 mmol, 4.0 equiv) and the reaction was stirred at 50° C. for 48 h. After the reaction was deemed complete (1H-NMR spectroscopy), the solvent was removed in vacuo and then repeatedly diluted with dichloromethane (3×30 mL) and the solvent removed in vacuo to yield tert-butyl(2-acetylphenyl)carbamate (2.08 g, 99%). This material was moved on without further purification. To a stirring solution of tert-butyl(2-acetylphenyl) carbamate (1.0 g, 4.25 mmol, 1.0 equiv) in methanol (28 mL, 0.15 M) at 0° C. was added sodium borohydride (0.117 g, 4.68 mmol, 1.1 equiv) portionwise with venting. The ice-bath was removed and the reaction was allowed to stir at room temperature for 2.5 h at which time the solvent was removed in vacuo. This material was diluted with water (DI, 30 mL), dichloromethane (30 mL), and transferred to a separatory funnel followed by acidification with aqueous hydrogen chloride (1.0 M, 5 mL). The organic portion was removed and the aqueous portion was back extracted with dichloromethane (2×20 mL). The organic layers were combined, dried over anhydrous sodium sulfate, and the solvent removed in vacuo to yield the crude alcohol (1.0 g, 99%). This material was used in the next step without further purification. The crude alcohol was taken up in dichloromethane (18 mL) and transferred to a 100 mL round bottom flask containing a magnetic stir-bar followed by cooling to 0° C. in an ice-bath. To this stirring solution was added sequentially pyridine (0.39 mL, 4.9 mmol, 1.1 equiv) and thionyl chloride (0.34 mL, 4.7 mmol, 1.05 equiv) drop-wise. The flask was removed from the ice-bath and allowed to stir at ambient temperature for 2.5 h at which time a 1:1 mixture of aqueous hydrogen chloride and water (1.0M HCl (aq)/DI water, 25 mL) was added with vigorous stirring. This mixture was transferred to a separatory funnel containing dichloromethane (20 mL). The organic portion was removed and the aqueous portion back extracted with dichloromethane (2×25 mL). The organic fractions were combined and washed with brine (20 mL), dried over anhydrous sodium sulfate, and the solvent removed in vacuo to yield the title compound as a red oil which was further purified by a short column of silica eluted with chloroform (200 mL) to yield SI-13 as a yellow crystalline solid (465 mg, 45%). Analytical data SI-13: $^1$H NMR (500 MHz, CDCl$_3$) δ 7.76 (d, J=7.4 Hz, 1H), 7.40 (d, J=7.8 Hz, 1H), 7.35-7.30 (m, 1H), 7.16-7.10 (m, 1H), 6.81 (s, 1H), 5.26 (q, J=6.8 Hz, 1H), 1.94 (d, J=6.9 Hz, 3H), 1.53 (s, 9H). $^{13}$C NMR (CDCl$_3$, 126 MHz) δ 153.3, 135.9, 132.2, 129.3, 126.0, 124.5, 123.8, 80.8, 55.1, 28.4, 23.7; IR (film) cm$^{-1}$ 3412, 3070, 2980, 2932, 1730, 1588, 1368, 1298, 1158, 1048, 759; Mp: 85-87° C.; LRMS (EI): Mass calcd for [M-tBuCl]$^+$ C$_9$H$_9$NO$_2$: 163.1; found 163.1.

Example 16

General Procedure for Reaction of Aryl Aldehydes with N-Boc Amino Benzyl Chlorides

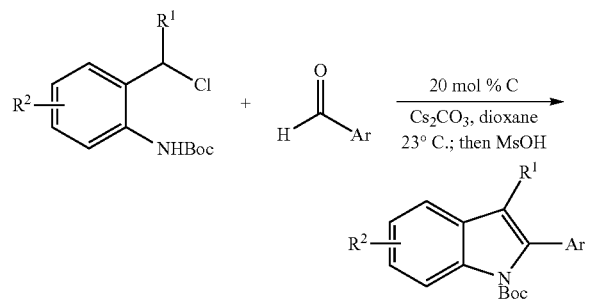

An oven-dried, screw-capped 2 dram vial equipped with a magnetic stirbar was taken into a nitrogen-filled drybox at which time benzyl chloride (0.32 mmol, 1.0 equiv), thiazolium salt C (0.064 mmol, 0.2 equiv), and cesium carbonate (0.38 mmol, 1.2 equiv) were added. The vial was capped with a septum cap, removed from the drybox and put under positive N$_2$ pressure. Into the vial were then successively added 1,4-dioxane (3.2 mL, 0.10 M) and aryl aldehyde (0.38 mmol, 1.2 equiv) via a syringe. The reaction was stirred at room temperature until consumption of the benzyl chloride was observed by $^1$H-NMR spectroscopy or for 36 h (usually complete within 36 h). The reaction mixture was opened to the atmosphere and methanesulfonic acid (0.150 mL, 6.5 equiv) was added dropwise with evolution of carbon dioxide. Once the intermediate ketone was consumed (*TLC, usually 5-60 min) the reaction was diluted with dichloromethane (3 mL) and transferred to separatory funnel containing aqueous sodium bicarbonate (1:1 sat. sodium bicarbonate/DI water, 10 mL). The reaction vessel was rinsed with dichloromethane (3×2 mL) and transferred to separatory funnel. After shaking vigorously with venting, the organic phase was separated and the aqueous phase was back extracted with dichloromethane (3×10 mL). The organic phases were combined, dried over anhydrous sodium sulfate, and the solvent removed in vacuo. Purification by flash chromatography with EtOAc/hexanes/dichloromethane (5%/35%/60%) afforded the corresponding indole. *Note: Exposure to anisaldehyde stain with heating provides the most conclusive TLC visualization. Intermediate ketone 3 and desired indole 4 have distinct colors (usually orange/red for 3 and dark red to purple/blue for 4, respectively). The indole product R$_f$ in 20% EtOAc/hexanes is consistently between 0.7-0.8 with substitution observed to have little effect on this behavior.

Example 17

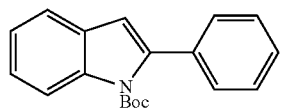

tert-butyl 2-phenyl-1H-indole-1-carboxylate (4): Prepared according to the general procedure starting from benzyl chloride (1) (78 mg, 0.32 mmol) and benzaldehyde (41 mg, 0.38 mmol). The unpurified residue was purified by column chromatography (5%/35%/60% EtOAc/hexanes/dichloromethane) to yield indole 4 as a white solid (77 mg, 82%). Analytical data 4: $^1$H NMR (500 MHz, CDCl$_3$) δ 8.29-8.18 (m, 1H), 7.58 (s, 1H), 7.47-7.31 (m, 6H), 7.27 (td, J=7.8, 1.3 Hz, 1H), 6.57 (s, 1H), 1.32 (s, 9H); $^{13}$C NMR (CDCl$_3$, 126 MHz) δ 150.1, 140.4, 137.3, 129.1, 128.6, 127.7, 127.5, 124.2, 122.8, 120.4, 115.1, 109.8, 83.3, 27.5; IR (film) cm$^{-1}$ 3063, 2979, 2931, 1730, 1589, 1454, 1369, 1225, 1159, 1134, 699; Mp: 70-72° C.; LRMS (ESI): Mass calcd for [M+H]$^+$ C$_{19}$H$_{20}$NO$_2$: 294.1; found 294.1.

Example 18

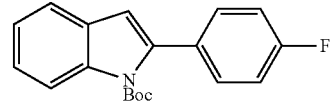

tert-butyl 2-(4-fluorophenyl)-1H-indole-1-carboxylate (4a): Prepared according to the general procedure starting from benzyl chloride (1) (78 mg, 0.32 mmol) and 4-flourobenzaldehyde (48 mg, 0.38 mmol). The unpurified residue was purified by column chromatography (5%/35%/60% EtOAc/hexanes/dichloromethane) to yield indole 4a as a tan solid (90 mg, 90%). Analytical data 4a: $^1$H NMR (500 MHz, CDCl$_3$) δ 8.23 (d, J=8.3 Hz, 1H), 7.68 (d, J=8.0 Hz, 2H), 7.60-7.52 (m, 3H), 7.37 (t, J=7.8 Hz, 1H), 7.28 (t, J=7.6 Hz, 1H), 6.62 (s, 1H), 1.34 (s, 9H); $^{13}$C NMR (CDCl$_3$, 126 MHz) δ 162.3 (d, J$_{C-F}$=247.0 Hz), 150.0, 139.3, 137.2, 131.0 (d, J$_{C-F}$=3.4 Hz), 130.3 (d, J$_{C-F}$=8.1 Hz), 129.0, 124.4, 122.9, 120.4, 115.2, 114.7 (d, J$_{C-F}$=21.6 Hz), 110.1, 83.5, 27.6; IR (film) cm$^{-1}$ 3063, 2982, 2933, 2361, 1734, 1619, 1324, 1225, 1068; Mp: 93-95° C.; LRMS (ESI): Mass calcd for [M+H]$^+$ C$_{19}$H$_{19}$FNO$_2$: 312.1; found 312.2.

Example 19

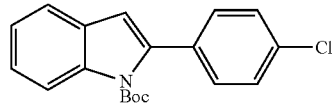 [SMILES: CC(C)(C)OC(=O)n1c(-c2ccc(Cl)cc2)cc2ccccc21]

tert-butyl 2-(4-chlorophenyl)-1H-indole-1-carboxylate (4b): Prepared according to the general procedure starting from benzyl chloride (1) (78 mg, 0.32 mmol) and 4-chlorobenzaldehyde (54 mg, 0.38 mmol). The unpurified residue was purified by column chromatography (5%/35%/60% EtOAc/hexanes/dichloromethane) to yield indole 4b as brown-yellow crystals (75 mg, 72%). Analytical data 4b: $^1$H NMR (500 MHz, CDCl$_3$) δ 8.21 (dd, J=8.5, 1.1 Hz, 1H), 7.59-7.55 (m, 1H), 7.37 (qd, J=8.5, 6.6 Hz, 5H), 7.29-7.24 (m, 1H), 6.56 (s, 1H), 1.37 (s, 9H); $^{13}$C NMR (CDCl$_3$, 126 MHz) δ 145.0, 139.1, 137.3, 133.5, 133.3, 129.9, 129.0, 127.9, 124.5, 123.0, 120.5, 115.2, 110.3, 83.7, 27.6; IR (film) cm$^{-1}$ 3068, 3052, 2979, 1732, 1451, 1368, 1326, 1158, 1131, 813, 744; Mp: 86-87° C.; LRMS (ESI): Mass calcd for [M+H]$^+$ C$_{19}$H$_{19}$ClNO$_2$: 328.1; found 328.1.

Example 20

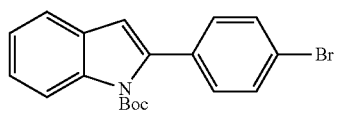 [SMILES: CC(C)(C)OC(=O)n1c(-c2ccc(Br)cc2)cc2ccccc21]

tert-butyl 2-(4-bromophenyl)-1H-indole-1-carboxylate (4c): Prepared according to the general procedure starting from benzyl chloride (1) (78 mg, 0.32 mmol) and 4-bromobenzaldehyde (71 mg, 0.38 mmol) at 50° C. for 12 h. The unpurified residue was purified by column chromatography (5%/35%/60% EtOAc/hexanes/dichloromethane) to yield indole 4c as a yellow solid (88 mg, 72%). Analytical data 4b: $^1$H NMR (500 MHz, CDCl$_3$) δ 8.22 (d, J=8.3 Hz, 1H), 7.56 (dd, J=9.6, 7.6 Hz, 3H), 7.36 (dd, J=8.4, 7.2, Hz, 1H), 7.33-7.27 (m, 3H), 6.57 (s, 1H), 1.38 (s, 9H); $^{13}$C NMR (CDCl$_3$, 126 MHz) δ 149.9, 139.1, 137.3, 133.8, 130.8, 130.1, 129.0, 124.5, 123.0, 121.6, 120.5, 115.2, 110.3, 83.7, 27.6; IR (film) cm$^{-1}$ 3056, 2980, 1733, 1452, 1325, 1224, 1160, 1133; Mp: 88-89° C.; LRMS (ESI): Mass calcd for [M+H]$^+$ C$_{19}$H$_{19}$BrNO$_2$: 372.1; found 372.1.

Example 21

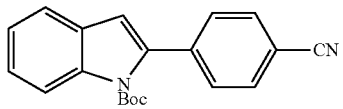 [SMILES: CC(C)(C)OC(=O)n1c(-c2ccc(C#N)cc2)cc2ccccc21]

tert-butyl 2-(4-cyanophenyl)-1H-indole-1-carboxylate (4d): Prepared according to the general procedure starting from benzyl chloride (1) (78 mg, 0.32 mmol) and 4-formylbenzonitrile (50 mg, 0.38 mmol). The unpurified residue was purified by column chromatography (5%/35%/60% EtOAc/hexanes/dichloromethane) to yield indole 4d as a white solid (62 mg, 61%). Analytical data 4b: $^1$H NMR (500 MHz, CDCl$_3$) δ 8.20 (d, J=8.4 Hz, 1H), 7.70 (d, J=8.3 Hz, 2H), 7.61-7.57 (m, 1H), 7.54 (d, J=8.2 Hz, 2H), 7.38 (ddd, J=8.5, 7.3, 1.3 Hz, 1H), 7.28 (td, J=7.5, 1.0 Hz, 1H), 6.64 (s, 1H), 1.38 (s, 9H); $^{13}$C NMR (CDCl$_3$, 126 MHz) δ 149.9, 139.5, 138.3, 137.7, 131.6, 129.2, 128.9, 125.2, 123.4, 120.9, 118.9, 115.5, 111.7, 111.1, 84.3, 27.7; IR (film) cm$^{-1}$ 3058, 2980, 2931, 2226, 1734, 1609, 1451, 1326, 1157, 1132; Mp: 114-116° C.; LRMS (EI): Mass calcd for [M-Boc]$^+$ C$_{15}$H$_{10}$N$_2$: 218.1; found 218.1.

Example 22

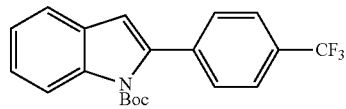 [SMILES: CC(C)(C)OC(=O)n1c(-c2ccc(C(F)(F)F)cc2)cc2ccccc21]

tert-butyl 2-(4-(trifluoromethyl)phenyl)-1H-indole-1-carboxylate (4e): Prepared according to the general procedure starting from benzyl chloride (1) (78 mg, 0.32 mmol) and 4-(trifluoromethyl)benzaldehyde (67 mg, 0.38 mmol). The unpurified residue was purified by column chromatography (5%/35%/60% EtOAc/hexanes/dichloromethane) to yield indole 4e as a white solid (60 mg, 52%). Analytical data 4e: $^1$H NMR (500 MHz, CDCl$_3$) δ 8.21 (d, J=8.3 Hz, 1H), 7.56 (d, J=7.7 Hz, 1H), 7.39 (dd, J=8.4, 5.3 Hz, 2H), 7.34 (t, J=7.9 Hz, 1H), 7.30-7.24 (m, 1H), 7.11 (t, J=8.5 Hz, 2H), 6.54 (s, 1H), 1.36 (s, 9H); $^{13}$C NMR (CDCl$_3$, 126 MHz) δ 149.9, 138.7, 138.5, 137.5, 129.5 (q, $J_{C-F}$=32.6 Hz), 128.91, 128.88, 124.8, 124.7 (q, $J_{C-F}$=3.7 Hz), 124.1 (q, $J_{C-F}$=271.9 Hz), 123.1, 120.7, 115.3, 111.0, 83.9, 27.5; IR (film) cm$^{-1}$ 3618, 2980, 2931, 2362, 1733, 1503, 1453, 1326, 1223, 1160, 1133; Mp: 108-109° C.; LRMS (EI): Mass calcd for [M+H]$^+$ C$_{20}$H$_{19}$F$_3$NO$_2$: 362.1; found 362.1.

Example 23

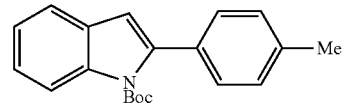 [SMILES: Cc1ccc(-c2cc3ccccc3n2C(=O)OC(C)(C)C)cc1]

tert-butyl 2-(p-tolyl)-1H-indole-1-carboxylate (4f): Prepared according to the general procedure starting from benzyl chloride (1) (78 mg, 0.32 mmol) and 4-methylbenzaldehyde (46 mg, 0.38 mmol). The unpurified residue was purified by column chromatography (5%/35%/60% EtOAc/hexanes/dichloromethane) to yield indole 4f as a brown oil (77 mg, 78%). Analytical data 4f: $^1$H NMR (500 MHz, CDCl$_3$) δ 8.23 (d, J=8.3 Hz, 1H), 7.58 (d, J=7.7 Hz, 1H), 7.35 (d, J=7.6 Hz, 3H), 7.31-7.21 (m, 3H), 6.56 (s, 1H), 2.44 (s, 3H), 1.38 (s, 9H); $^{13}$C NMR (CDCl$_3$, 126 MHz) δ 150.3, 140.7, 137.4, 137.4, 132.0, 129.3, 128.6, 128.5, 124.2, 122.9, 120.4, 115.2, 109.7, 83.4, 27.7, 21.4; IR (film) cm$^{-1}$; 3054, 2979, 2931, 2365, 1731, 1457, 1327, 1161, 852, 747; LRMS (EI) Mass calcd for [M-Boc]$^+$ C$_{15}$H$_{12}$N: 307.4; found 307.0.

Example 24

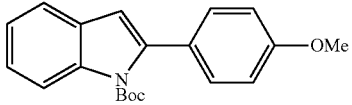 [SMILES: COc1ccc(-c2cc3ccccc3n2C(=O)OC(C)(C)C)cc1]

tert-butyl 2-(4-methoxyphenyl)-1H-indole-1-carboxylate (4g): Prepared according to the general procedure starting from benzyl chloride (1) (78 mg, 0.32 mmol) and 4-methoxybenzaldehyde (53 mg, 0.38 mmol). The unpurified residue was purified by column chromatography (5%/

35%/60% EtOAc/hexanes/dichloromethane) to yield indole 4g as a off-white solid (63 mg, 61%). Analytical data 4g: $^1$H NMR (500 MHz, CDCl$_3$) δ 8.19 (d, J=8.3 Hz, 1H), 7.54 (dd, J=7.7, 1.3 Hz, 1H), 7.35 (d, J=8.6 Hz, 2H), 7.32 (ddd, J=8.5, 7.3, 1.3 Hz, 1H), 7.27-7.21 (m, 1H), 6.95 (d, J=8.7 Hz, 2H), 6.51 (s, 1H), 3.86 (s, 3H), 1.37 (s, 9H); $^{13}$C NMR (CDCl$_3$, 126 MHz) δ 159.1, 150.2, 140.3, 137.2, 129.8, 129.2, 127.3, 124.0, 122.8, 120.2, 115.1, 113.2, 109.4, 83.3, 55.3, 27.6; IR (film) cm$^{-1}$ 3050, 2679, 2932, 2349, 1729, 1612, 1505, 1452, 1329, 1247, 1132; Mp: 89-90° C.; LRMS (ESI): Mass calcd for [M+H]$^+$ C$_{20}$H$_{22}$NO$_3$: 324.2; found 324.2.

Example 25

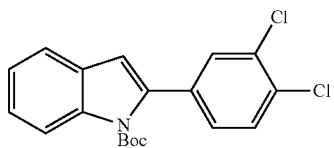 [SMILES: CC(C)(C)OC(=O)n1c(-c2ccc(Cl)c(Cl)c2)cc2ccccc21]

tert-butyl 2-(3,4-dichlorophenyl)-1H-indole-1-carboxylate (4h): Prepared according to the general procedure starting from benzyl chloride (1) (78 mg, 0.32 mmol) and 3,4-dichlorobenzaldehyde (123 mg, 0.38 mmol). The amount of aryl aldehyde was increased from 1.2 equiv to 2.2 equiv. The unpurified residue was purified by column chromatography (5%/35%/60% EtOAc/hexanes/dichloromethane) to yield indole 4h as a light-yellow oil (105 mg, 91%). Analytical data 4h: $^1$H NMR (500 MHz, CDCl$_3$) δ 8.23 (d, J=8.4 Hz, 1H), 7.59 (d, J=7.7 Hz, 1H), 7.55 (d, J=2.0 Hz, 1H), 7.51 (d, J=8.3 Hz, 1H), 7.43-7.38 (m, 1H), 7.33-7.28 (m, 2H), 6.62 (s, 1H), 1.42 (s, 9H); $^{13}$C NMR (CDCl$_3$, 126 MHz) δ 149.8, 137.7, 137.4, 134.7, 131.8, 131.6, 130.5, 129.7, 128.8, 127.8, 124.8, 123.1, 120.6, 115.3, 110.9, 84.0, 27.6; IR (film) cm$^{-1}$ 3061, 2980, 2931, 1734, 1651, 1450, 1324, 1030; LRMS (ESI): Mass calcd for [M+H]$^+$ C$_{19}$H$_{18}$Cl$_2$NO$_2$: 362.1; found 362.1.

Example 26

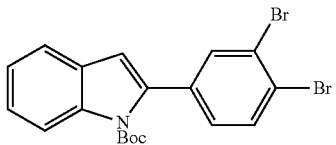

tert-butyl 2-(3,4-dibromophenyl)-1H-indole-1-carboxylate (4i): Prepared according to the general procedure starting from benzyl chloride (1) (78 mg, 0.32 mmol) and 3,4-dibromobenzaldehyde (101 mg, 0.38 mmol). Reaction temperature was raised to 50° C. The unpurified residue was purified by column chromatography (5%/35%/60% EtOAc/hexanes/dichloromethane) to yield indole 4i as a yellow oil (116 mg, 80%). Analytical data 4i: $^1$H NMR (500 MHz, CDCl$_3$) δ 8.23 (dd, J=8.4, 1.1 Hz, 1H), 7.70 (d, J=2.0 Hz, 1H), 7.66 (d, J=8.2 Hz, 1H), 7.57 (dt, J=7.9, 1.0 Hz, 1H), 7.37 (ddd, J=8.5, 7.2, 1.3 Hz, 1H), 7.28 (td, J=7.6, 1.1 Hz, 1H), 7.25 (dd, J=8.2, 2.1 Hz, 1H), 6.60 (s, 1H), 1.41 (s, 9H); $^{13}$C NMR (CDCl$_3$, 126 MHz) δ 149.7, 137.5, 137.4, 135.4, 133.6, 132.8, 128.8, 128.5, 124.8, 124.0, 123.6, 123.1, 120.6, 115.3, 110.9, 84.0, 27.6; IR (film) cm$^{-1}$ 3055, 2979, 2932, 1733, 1448, 1324, 1160, 813, 744; LRMS (ESI): Mass calcd for [M+H]$^+$ C$_{19}$H$_{18}$Br$_2$NO$_2$: 449.0; found 449.0.

Example 27

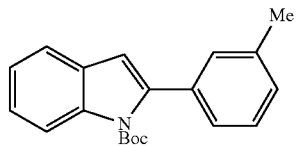 [SMILES: Cc1cccc(-c2cc3ccccc3n2C(=O)OC(C)(C)C)c1]

tert-butyl 2-(m-tolyl)-1H-indole-1-carboxylate (4j): Prepared according to the general procedure starting from benzyl chloride (1) (78 mg, 0.32 mmol) and 3-methylbenzaldehyde (46 mg, 0.38 mmol). The unpurified residue was purified by column chromatography (5%/35%/60% EtOAc/hexanes/dichloromethane) to yield indole 4j as a brown oil (87 mg, 88%). Analytical data 4j: $^1$H NMR (500 MHz, CDCl$_3$) δ 8.21 (dd, J=8.2, 1.1 Hz, 1H), 7.59-7.52 (m, 1H), 7.33 (ddd, J=8.4, 7.2, 1.4 Hz, 1H), 7.32-7.28 (m, 1H), 7.28-7.22 (m, 3H), 7.18 (d, J=7.2 Hz, 1H), 6.56 (s, 1H), 2.41 (s, 3H), 1.32 (s, 9H); $^{13}$C NMR (CDCl$_3$, 126 MHz) δ 150.2, 140.6, 137.3, 137.1, 134.7, 129.4, 129.1, 128.2, 127.7, 125.7, 124.1, 122.8, 120.3, 115.0, 109.6, 83.2, 27.5, 21.3; IR (film) cm$^{-1}$ 3053, 2978, 2360, 2340, 1730, 1453, 1367, 1326, 849, 813, 770, 701; LRMS (ESI): Mass calcd for [M+H]$^+$ C$_{20}$H$_{22}$NO$_2$: 308.2; found 308.2.

Example 28

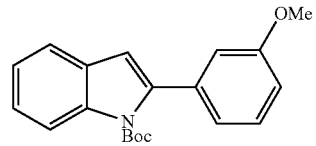 [SMILES: COc1cccc(-c2cc3ccccc3n2C(=O)OC(C)(C)C)c1]

tert-butyl 2-(3-methoxyphenyl)-1H-indole-1-carboxylate (4k): Prepared according to the general procedure starting from benzyl chloride (1) (78 mg, 0.32 mmol) and 3-methoxybenzaldehyde (52 mg, 0.38 mmol). The unpurified residue was purified by column chromatography (5%/35%/60% EtOAc/hexanes/dichloromethane) to yield indole 4k as a yellow oil (76 mg, 73%). Analytical data 4k: $^1$H NMR (500 MHz, CDCl$_3$) δ 8.23 (d, J=8.3 Hz, 1H), 7.57 (d, J=7.7 Hz, 1H), 7.37-7.34 (m, 1H), 7.34-7.31 (m, 1H), 7.29-7.25 (m, 1H), 7.06-7.02 (m, 1H), 7.00-6.98 (m, 1H), 6.93 (dd, J=8.3, 2.6 Hz, 1H), 6.59 (s, 1H), 3.85 (s, 3H), 1.35 (s, 9H); $^{13}$C NMR (CDCl$_3$, 126 MHz) δ 159.0, 150.1, 140.2, 137.3, 136.1, 129.0, 128.7, 124.2, 122.8, 121.2, 120.4, 115.0, 114.2, 113.2, 109.8, 83.3, 55.2, 27.5; IR (film) cm$^{-1}$ 3056, 2978, 2835, 1731, 1454, 1327, 1215, 1161, 1051, 850, 749; LRMS (ESI): Mass calcd for [M+H]$^+$ C$_{20}$H$_{22}$NO$_3$: 324.2; found 324.2.

Example 29

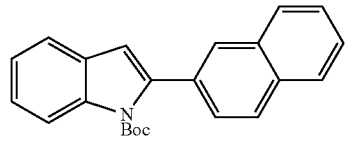 [SMILES: CC(C)(C)OC(=O)n1c(-c2ccc3ccccc3c2)cc2ccccc21]

tert-butyl 2-(naphthalen-2-yl)-1H-indole-1-carboxylate (4l): Prepared according to the general procedure starting from benzyl chloride (1) (78 mg, 0.32 mmol) and 2-napthaldehyde (60 mg, 0.38 mmol). The unpurified residue was purified by column chromatography (5%/35%/60% EtOAc/hexanes/dichloromethane) to yield indole 4l as a pale-yellow solid (87 mg, 79%). Analytical data 4l: $^1$H NMR (500 MHz, CDCl$_3$) δ 8.30 (dd, J=8.3, 1.1 Hz, 1H), 7.96 (d, J=1.7 Hz, 1H), 7.93-7.86 (m, 3H), 7.62 (dd, J=7.7, 1.2 Hz, 1H), 7.55 (ddd, J=11.9, 7.1, 2.0 Hz, 3H), 7.40 (ddd, J=8.4, 7.2, 1.3 Hz, 1H), 7.31 (td, J=7.5, 1.1 Hz, 1H), 6.70 (s, 1H), 1.29 (s, 9H); $^{13}$C NMR (CDCl$_3$, 126 MHz) δ 150.2, 140.4, 137.5, 132.9, 132.5, 132.3, 129.2, 127.9, 127.6, 127.1, 127.0, 126.9, 126.3, 126.1, 124.3, 122.9, 120.4, 115.2, 110.3, 83.5, 27.5; IR (film) cm$^{-1}$ 3056, 2679, 2361, 1730, 1451, 1328, 1158; Mp: 134-135° C.; LRMS (ESI): Mass calcd for [M+H]$^+$ C$_{23}$H$_{22}$NO$_2$: 344.2; found 344.2.

Example 30

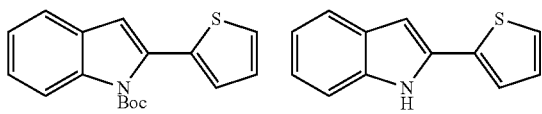

tert-butyl 2-(thiophen-2-yl)-1H-indole-1-carboxylate (4n) & 2-(thiophen-2-yl)-1H-indole (SI-14): Prepared according to the general procedure starting from benzyl chloride (1) (78 mg, 0.32 mmol) and thiophene-2-carbaldehyde (43 mg, 0.38 mmol). The unpurified residue was purified by column chromatography (20%/80% EtOAc/hexanes) to yield indole 4n as a pale-yellow oil (49 mg, 51%) and N—H indole SI-14 as an off-white solid (25 mg, 39%). Analytical data 4n: $^1$H NMR (500 MHz, CDCl$_3$) δ 8.21 (d, J=8.4 Hz, 1H), 7.55 (d, J=7.7 Hz, 1H), 7.38 (dd, J=5.1, 1.0 Hz, 1H), 7.37-7.33 (m, 1H), 7.28-7.23 (m, 1H), 7.12 (dd, J=3.5, 1.0 Hz, 1H), 7.07 (dd, J=5.1, 3.6 Hz, 1H), 6.69 (s, 1H), 1.43 (s, 9H); $^{13}$C NMR (CDCl$_3$, 126 MHz) δ 149.9, 137.3, 135.4, 132.5, 128.7, 127.5, 126.5, 125.8, 124.6, 122.9, 120.4, 115.2, 111.8, 83.5, 27.58; IR (film) cm$^{-1}$ 3108, 3070, 2978, 2931, 1730, 1474, 1329, 1160, 1105, 1000, 747, 698; LRMS (ESI): Mass calcd for [M+H]$^+$ C$_{17}$H$_{18}$NO$_2$S: 300.1; found 300.1. Analytical data for SI-14 matches previously reported characterization data.

Example 31

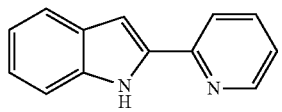 [SMILES: c1ccc(-c2cc3ccccc3[nH]2)nc1]

tert-butyl 2-(thiophen-2-yl)-1H-indole-1-carboxylate (4m): Prepared according to the general procedure starting from benzyl chloride (1) (78 mg, 0.32 mmol) and picolinaldehyde (41 mg, 0.38 mmol). Cyclization and deacylation occurred concomitantly over a 14 h period. The unpurified residue was purified by column chromatography (30%/70% EtOAc/hexanes) to yield indole 4m as an off-white solid (55 mg, 88%). Analytical data for 4m matches previously reported characterization data.

Example 32

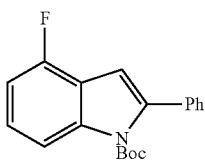 [SMILES: CC(C)(C)OC(=O)n1c(-c2ccccc2)cc2c(F)cccc21]

tert-butyl 4-fluoro-2-phenyl-1H-indole-1-carboxylate (4p): Prepared according to the general procedure starting from 3-fluoro-amino-benzyl chloride SI-5 (83 mg, 0.32 mmol) and benzaldehyde (41 mg, 0.38 mmol). The unpurified residue was purified by column chromatography (5%/35%/60% EtOAc/hexanes/dichloromethane) to yield indole 4p as a orange-brown solid (86 mg, 86%). Analytical data 4p: $^1$H NMR (500 MHz, CDCl$_3$) δ 8.01 (d, J=8.3 Hz, 1H), 7.45-7.35 (m, 5H), 7.26 (td, J=8.3, 5.4 Hz, 1H), 6.99-6.91 (m, 1H), 6.67 (s, 1H), 1.31 (s, 9H); $^{13}$C NMR (CDCl$_3$, 126 MHz) δ 156.5, 154.5, 149.9, 140.4, 139.4 (d, J$_{C-F}$=9.7 Hz), 134.4, 128.7, 127.8 (d, J$_{C-F}$=3.1 Hz), 124.8 (d, J$_{C-F}$=7.4 Hz), 118.0 (d, J$_{C-F}$=22.3 Hz), 111.1 (d, J$_{C-F}$=3.6 Hz), 108.0 (d, J$_{C-F}$=18.4 Hz), 105.0, 83.8, 27.4; IR (film) cm$^{-1}$ 3063, 2982, 2361, 1735, 1480, 1368, 1337, 1145; Mp: 121-122° C.; LRMS (ESI): Mass calcd for [M+H]$^+$ C$_{19}$H$_{19}$FNO$_2$: 312.1; found 312.1.

Example 33

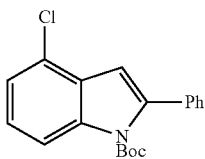 [SMILES: CC(C)(C)OC(=O)n1c(-c2ccccc2)cc2c(Cl)cccc21]

tert-butyl 4-chloro-2-phenyl-1H-indole-1-carboxylate (4q): Prepared according to the general procedure starting from 3-chloro-amino-benzyl chloride SI-9 (88 mg, 0.32 mmol) and benzaldehyde (41 mg, 0.38 mmol). The unpurified residue was purified by column chromatography (5%/35%/60% EtOAc/hexanes/dichloromethane) to yield indole 4q as a tan solid (92 mg, 88%). Analytical data 4q: $^1$H NMR (500 MHz, CDCl$_3$) δ 7.97 (dd, J=5.7, 3.6 Hz, 1H), 7.33-7.19 (m, 5H), 7.18-6.99 (m, 2H), 6.54 (s, 1H), 1.14 (s, 9H); $^{13}$C NMR (CDCl$_3$, 126 MHz) δ 149.8, 141.0, 138.0, 134.3, 128.6, 127.84, 127.80, 127.78, 125.6, 124.8, 122.5, 113.6, 107.7, 83.9, 27.4; IR (film) cm$^{-1}$ 3061, 2980, 2931, 1736, 1426, 1368, 1326, 1134, 779; Mp: 111-112° C.; LRMS (ESI): Mass calcd for [M+H]$^+$ C$_{19}$H$_{19}$ClNO$_2$: 328.1; found 328.1.

Example 34

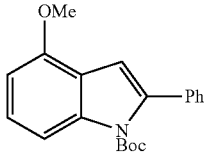 [SMILES: COc1cccc2c1cc(-c1ccccc1)n2C(=O)OC(C)(C)C]

tert-butyl 4-methoxy-2-phenyl-1H-indole-1-carboxylate (4r): Prepared according to the general procedure starting from 3-methoxy-amino-benzyl chloride SI-8 (87 mg, 0.32 mmol) and benzaldehyde (41 mg, 0.38 mmol). The unpurified residue was purified by column chromatography (5%/35%/60% EtOAc/hexanes/dichloromethane) to yield indole 4r as an off-white solid (95 mg, 92%). Analytical data 4r: $^1$H NMR (500 MHz, CDCl$_3$) δ 7.84 (d, J=8.4 Hz, 1H), 7.50-7.33 (m, 5H), 7.28 (t, J=8.3 Hz, 1H), 6.71 (d, J=7.9 Hz, 1H), 6.71 (s, 1H), 3.96 (s, 3H), 1.32 (s, 9H); $^{13}$C NMR (CDCl$_3$, 126 MHz) δ 152.6, 150.2, 138.9, 138.6, 134.9, 128.6, 127.7, 127.3, 125.0, 119.4, 108.2, 106.7, 103.1, 83.3, 55.4, 27.5; IR (film) cm$^{-1}$ 3066, 2977, 2932, 2362, 1731, 1435, 1330, 1262, 1142, 779; Mp: 81-82° C.; LRMS (ESI): Mass calcd for [M+H]$^+$ C$_{20}$H$_{22}$NO$_3$: 324.2; found 324.2.

Example 35

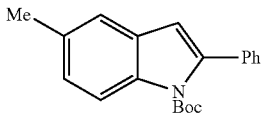 [SMILES: Cc1ccc2c(c1)cc(-c1ccccc1)n2C(=O)OC(C)(C)C]

tert-butyl 5-methyl-2-phenyl-1H-indole-1-carboxylate (4t): Prepared according to the general procedure starting from 4-methyl-amino-benzyl chloride SI-7 (XX mg, 0.32 mmol) and benzaldehyde (41 mg, 0.38 mmol). The unpurified residue was purified by column chromatography (5%/35%/60% EtOAc/hexanes/dichloromethane) to yield indole 4t as a orange oil (90 mg, 91%). Analytical data 4t: $^1$H NMR (500 MHz, CDCl$_3$) δ 8.09 (d, J=8.5 Hz, 1H), 7.39 (ddd, J=24.5, 9.9, 8.1 Hz, 6H), 7.18-7.13 (m, 1H), 6.49 (s, 1H), 2.46 (s, 3H), 1.31 (s, 9H); $^{13}$C NMR (CDCl$_3$, 126 MHz) δ 150.2, 140.5, 135.6, 135.0, 132.3, 129.3, 128.6, 127.7, 127.4, 125.6, 120.4, 114.8, 109.7, 83.1, 27.5, 21.2; IR (film) cm$^{-1}$ 3060, 3026, 2979, 2930, 2868, 1729, 1607, 1470, 1320, 766, 698, 638; LRMS (ESI): Mass calcd for [M+H]$^+$ C$_{20}$H$_{22}$NO$_2$: 308.2; found 308.2.

Example 36

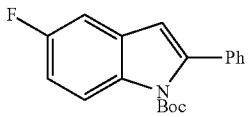 [SMILES: CC(C)(C)OC(=O)n1c(-c2ccccc2)cc2cc(F)ccc21]

tert-butyl 5-fluoro-2-phenyl-1H-indole-1-carboxylate (4s): Prepared according to the general procedure starting from 4-fluoro-amino-benzyl chloride SI-4 (83 mg, 0.32 mmol) and benzaldehyde (41 mg, 0.38 mmol). The unpurified residue was purified by column chromatography (5%/35%/60% EtOAc/hexanes/dichloromethane) to yield indole 4s as a yellow oil (88 mg, 88%). Analytical data 4s: $^1$H NMR (500 MHz, CDCl$_3$) δ 8.20 (dd, J=9.1, 4.6 Hz, 1H), 7.43 (d, J=4.5 Hz, 4H), 7.41-7.38 (m, 1H), 7.22 (dd, J=8.7, 2.6 Hz, 1H), 7.07 (td, J=9.1, 2.6 Hz, 1H), 6.52 (s, 1H), 1.31 (s, 9H); $^{13}$C NMR (CDCl$_3$, 126 MHz) δ 160.2, 158.3, 149.9, 141.9, 134.6, 133.6, 129.8 (d, $J_{C-F}$=10.0 Hz), 128.6, 127.7 (d, $J_{C-F}$=2.7 Hz), 116.1 (d, $J_{C-F}$=9.0 Hz), 111.8 (d, $J_{C-F}$=24.9 Hz), 109.4 (d, $J_{C-F}$=3.9 Hz), 105.7 (d, $J_{C-F}$=23.7 Hz), 83.5, 27.4; IR (film) cm$^{-1}$ 3047, 2980, 2932, 2361, 2341, 1730, 1467, 1157, 1118, 848; LRMS (ESI): Mass calcd for [M+H]$^+$ C$_{19}$H$_{19}$FNO$_2$: 312.1; found 312.1.

Example 37

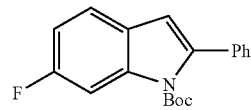

tert-butyl 6-fluoro-2-phenyl-1H-indole-1-carboxylate (4u): Prepared according to the general procedure starting from 5-fluoro-amino-benzyl chloride SI-3 (XX mg, 0.32 mmol) and benzaldehyde (41 mg, 0.38 mmol). The unpurified residue was purified by column chromatography (5%/35%/60% EtOAc/hexanes/dichloromethane) to yield indole 4u as a orange oil (84 mg, 84%). Analytical data 4u: $^1$H NMR (500 MHz, CDCl$_3$) δ 7.96 (dd, J=10.6, 2.3 Hz, 1H), 7.46 (dd, J=8.5, 5.5 Hz, 1H), 7.42-7.33 (m, 5H), 7.01 (td, J=8.9, 2.4 Hz, 1H), 6.52 (s, 1H), 1.30 (s, 9H); $^{13}$C NMR (CDCl$_3$, 126 MHz) δ 161.8, 159.9, 150.0, 140.8 (d, $J_{C-F}$=4.0 Hz), 137.6 (d, $J_{C-F}$=12.9 Hz), 134.7, 128.7, 127.7, 125.4, 121.0 (d, $J_{C-F}$=9.8 Hz), 111.1 (d, $J_{C-F}$=24.2 Hz), 109.4, 102.7 (d, $J_{C-F}$=28.8 Hz), 83.8, 27.5; IR (film) cm$^{-1}$ 3066, 2981, 2932, 1733, 1483, 1367, 1331, 1223, 1158, 1134; LRMS (EI): Mass calcd for [M-Boc]$^+$ C$_{14}$H$_{14}$FN: 211.1; found 211.1.

Example 38

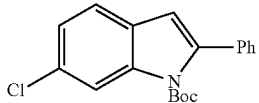

tert-butyl 6-chloro-2-phenyl-1H-indole-1-carboxylate (4v): Prepared according to the general procedure starting from 5-chloro-amino-benzyl chloride SI-11 (88 mg, 0.32 mmol) and benzaldehyde (41 mg, 0.38 mmol). The unpurified residue was purified by column chromatography (5%/35%/60% EtOAc/hexanes/dichloromethane) to yield indole 4v as a yellow solid (84 mg, 80%). Analytical data 4v: $^1$H NMR (500 MHz, CDCl$_3$) δ 8.28 (d, J=1.9 Hz, 1H), 7.46 (d, J=8.2 Hz, 1H), 7.43-7.35 (m, 5H), 7.24 (dd, J=8.3, 1.9 Hz, 1H), 6.52 (s, 1H), 1.30 (s, 9H); $^{13}$C NMR (CDCl$_3$, 126 MHz) δ 149.8, 141.0, 137.7, 134.4, 130.0, 128.6, 127.8, 127.7, 127.5, 123.4, 121.0, 115.4, 109.3, 83.8, 27.4; IR (film) cm$^{-1}$ 3113, 3062, 2980, 2932, 1733, 1455, 1323, 1224, 1158, 768; Mp: 61-62° C.; LRMS (ESI): Mass calcd for [M+H]$^+$ C$_{19}$H$_{19}$ClNO$_2$: 328.1; found 328.1.

Example 39

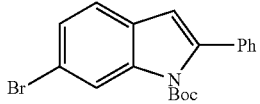 [SMILES: CC(C)(C)OC(=O)n1c(-c2ccccc2)cc2ccc(Cl)cc21]

tert-butyl 6-bromo-2-phenyl-1H-indole-1-carboxylate (4w): Prepared according to the general procedure starting from 5-bromo-amino-benzyl chloride SI-12 (103 mg, 0.32 mmol) and benzaldehyde (41 mg, 0.38 mmol). The unpurified residue was purified by column chromatography (5%/35%/60% EtOAc/hexanes/dichloromethane) to yield indole 4w as a red solid (98 mg, 82%). Analytical data 4w: $^1$H NMR (500 MHz, CDCl$_3$) δ 8.53-8.38 (m, 1H), 7.49-7.35 (m, 7H), 6.52 (s, 1H), 1.31 (s, 9H); $^{13}$C NMR (CDCl$_3$, 126 MHz) δ 149.7, 140.9, 138.0, 134.4, 128.6, 127.9, 127.8, 127.7, 126.1, 121.4, 118.3, 117.8, 109.4, 83.9, 27.4; IR (film) cm$^{-1}$ 2980, 2932, 1733, 1452, 1369, 1321, 1224, 1158, 698; Mp: 54-55° C.; LRMS (ESI): Mass calcd for [M+H]$^+$ C$_{19}$H$_{19}$BrNO$_2$: 372.1; found 372.1.

Example 40

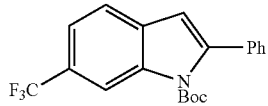

tert-butyl 2-phenyl-6-(trifluoromethyl)-1H-indole-1-carboxylate (4x): Prepared according to the general procedure starting from 5-(trifluoromethyl)-amino-benzyl chloride SI-2 (99 mg, 0.32 mmol) and benzaldehyde (41 mg, 0.38 mmol). The unpurified residue was purified by column chromatography (5%/35%/60% EtOAc/hexanes/dichloromethane) to yield indole 4x as a off-white solid (87 mg, 84%). Analytical data 4x: $^1$H NMR (500 MHz, CDCl$_3$) δ 8.56 (s, 1H), 7.64 (d, J=8.2 Hz, 1H), 7.52-7.49 (m, 1H), 7.43 (d, J=4.4 Hz, 5H), 6.60 (s, 1H), 1.32 (s, 9H); $^{13}$C NMR (CDCl$_3$, 126 MHz) δ 149.7, 143.0, 136.4, 134.2, 131.5, 128.7, 128.0, 127.8, 126.1 (q, J$_{C-F}$=31.9 Hz), 123.8, 120.6, 119.6 (q, J$_{C-F}$=3.7 Hz), 112.8 (q, J$_{C-F}$=4.5 Hz), 109.3, 84.2, 27.4; IR (film) cm$^{-1}$ 3064, 2981, 2936, 1736, 1438, 1335, 1226, 1158; Mp: 104° C.; LRMS (ESI): Mass calcd for [M+H]$^+$ C$_{20}$H$_{19}$F$_3$NO$_2$: 362.1; found 362.1.

Example 4L

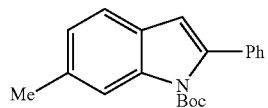 [SMILES: Cc1ccc2cc(-c3ccccc3)n(C(=O)OC(C)(C)C)c2c1]

tert-butyl 6-methyl-2-phenyl-1H-indole-1-carboxylate (4y): Prepared according to the general procedure starting from 5-methyl-amino-benzyl chloride SI-6 (84 mg, 0.32 mmol) and benzaldehyde (41 mg, 0.38 mmol). The unpurified residue was purified by column chromatography (5%/35%/60% EtOAc/hexanes/dichloromethane) to yield indole 4y as a yellow solid (61 mg, 60%). Analytical data 4y: $^1$H NMR (500 MHz, CDCl$_3$) δ 8.09 (s, 1H), 7.45 (d, J=8.0 Hz, 1H), 7.43-7.33 (m, 5H), 7.10 (d, J=7.9 Hz, 1H), 6.52 (s, 1H), 2.53 (s, 3H), 1.30 (s, 9H); $^{13}$C NMR (CDCl$_3$, 126 MHz) δ 150.3, 139.7, 137.8, 135.1, 134.3, 128.6, 127.7, 127.3, 126.8, 124.3, 119.9, 115.3, 109.8, 83.1, 27.4, 22.0; IR (film) cm$^{-1}$ 3037, 2978, 2922, 2361, 2341, 1732, 1325, 1221, 680; Mp: 62-64° C.; LRMS (ESI): Mass calcd for [M+H]$^+$ C$_{20}$H$_{22}$NO$_2$: 308.2; found.

Example 42

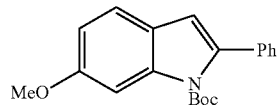 [SMILES: COc1ccc2cc(-c3ccccc3)n(C(=O)OC(C)(C)C)c2c1]

tert-butyl 6-methoxy-2-phenyl-1H-indole-1-carboxylate (4z): Prepared according to the general procedure starting from 5-methoxy-amino-benzyl chloride SI-10 (87 mg, 0.32 mmol) and benzaldehyde (41 mg, 0.38 mmol). The unpurified residue was purified by column chromatography (5%/35%/60% EtOAc/hexanes/dichloromethane) to yield indole 4z as a yellow oil (27 mg, 26%). Analytical data 4z: $^1$H NMR (500 MHz, CDCl$_3$) 1H NMR (500 MHz, Chloroform-d) δ 7.83 (d, J=2.3 Hz, 1H), 7.43 (d, J=8.5 Hz, 1H), 7.41-7.32 (m, 5H), 6.91 (dd, J=8.5, 2.4 Hz, 1H), 3.92 (s, 3H), 1.30 (s, 9H); $^{13}$C NMR (CDCl$_3$, 126 MHz) δ 157.7, 150.3, 139.2, 138.4, 135.1, 128.5, 127.7, 127.2, 122.9, 120.8, 112.3, 109.7, 99.2, 83.2, 55.6, 27.4; IR (film) cm$^{-1}$ 3066, 2977, 2929, 1729, 1489, 1327, 1161, 1040, 839; LRMS (ESI): Mass calcd for [M+H]$^+$ C$_{20}$H$_{22}$NO$_3$: 324.2; found 324.2.

Example 43

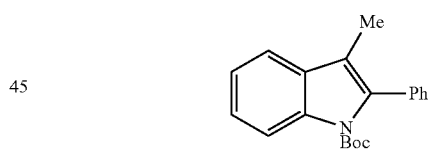

tert-butyl 3-methyl-2-phenyl-1H-indole-1-carboxylate (4aa): Prepared according to the general procedure starting from tert-butyl (2-(1-chloroethyl)phenyl)carbamate SI-13 (82 mg, 0.32 mmol) and benzaldehyde (41 mg, 0.38 mmol). The unpurified residue was purified by column chromatography (20%/80% EtOAc/hexanes) to yield indole 4aa as an orange solid (90 mg, 91%). Analytical data 4aa: $^1$H NMR (500 MHz, CDCl$_3$) δ 8.25 (d, J=8.2 Hz, 1H), 7.53 (d, J=7.7 Hz, 1H), 7.43 (t, J=7.4 Hz, 2H), 7.39-7.26 (m, 5H), 2.14 (s, 3H), 1.24 (s, 9H); $^{13}$C NMR (CDCl$_3$, 126 MHz) δ 150.3, 136.5, 135.6, 134.5, 130.4, 129.8, 127.8, 127.3, 124.5, 122.6, 118.7, 116.3, 115.1, 82.8, 27.5, 9.2; IR (film) cm$^{-1}$ 3054, 3032, 2978, 2931, 1726, 1456, 1355, 1330, 1155, 1081, 830, 752, 700; Mp: 110-112° C.; LRMS (ESI): Mass calcd for [M+H]$^+$ C$_{20}$H$_{22}$NO$_2$: 307.4; found 307.4.

Example 44

Synthesis of Exelixis c-Kit Inhibitor

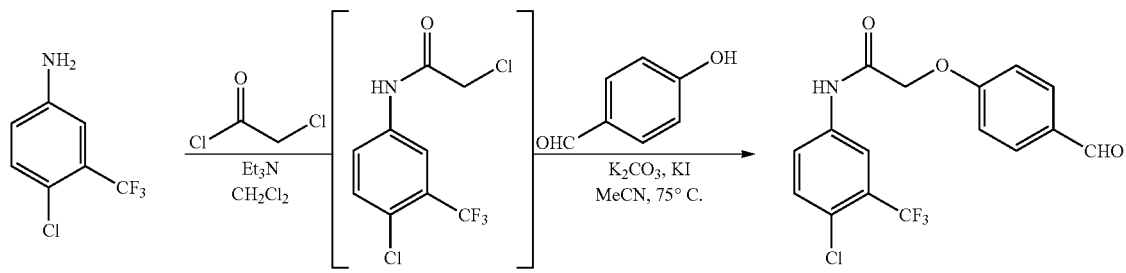

N-(4-chloro-3-(trifluoromethyl)phenyl)-2-(4-formylphenoxyl)acetamide (6). To a stirring solution of chloroacetyl chloride (0.516 mL, 6.44 mmol, 1.05 equiv) at 0° C. in dichloromethane (24.5 mL) was added drop-wise a solution of 4-chloro-3-(trifluoromethyl)aniline (1.20 g, 6.14 mmol, 1.0 equiv) in dichloromethane (5 mL). The icebath was removed and the reaction was stirred for 1.5 h until consumption of the aniline was observed by $^1$H-NMR spectroscopy. The reaction was quenched with water (25 mL). The crude mixture was transferred to a separatory funnel and the organic portion removed followed by further extraction of the aqueous phase with dichloromethane (2×20 mL). The combined organic fractions were washed with brine (20 mL), dried over anhydrous sodium sulfate, and the solvent removed in vacuo to yield the amide as a brown oil (1.66 g, 99%). This material was used in the next step without further purification. The amide was taken up in acetonitrile (24.4 mL) and transferred to a 100 mL round bottom flask with magnetic stir bar. To this stirring solution was added sequentially potassium carbonate (1.69 g, 12.2 mmol, 2.0 equiv), potassium iodide (1.064 g, 6.41 mmol, 1.05 equiv), and 4-hydroxybenzaldehyde (0.745 g, 7.67 mmol, 1 equiv) freshly recrystallized from boiling water. The flask was fitted with an air condenser, heated to 75° C. and stirred for 12 h. Once consumption of the aldehyde was observed by $^1$H-NMR spectroscopy, the reaction mixture was cooled and the solvent removed in vacuo to yield crude solid. The crude mixture was diluted with chloroform (50 mL), water (DI, 30 mL), and aqueous HCl (1.0 M, 10 mL) followed by transfer to a separatory funnel. The organic portion was removed and the aqueous phase was back extracted with chloroform (2×30 mL). The organic fractions were combined, washed with brine (30 mL), and dried over anhydrous sodium sulfate followed by removal of solvent in vacuo to yield aldehyde 6 as a reddish tan solid (2.10 g, 95% yield over two steps) not requiring any further purification. Analytical data 6: $^1$H NMR (500 MHz, CDCl$_3$) 1H NMR (500 MHz, Chloroform-d) δ 9.95 (s, 1H), 8.32 (s, 1H), 7.94-7.90 (m, 3H), 7.84 (dd, J=8.7, 2.5 Hz, 1H), 7.50 (d, J=8.7 Hz, 1H), 7.13 (d, J=8.7 Hz, 2H), 4.72 (s, 2H); $^{13}$C NMR (CDCl$_3$, 126 MHz) δ 190.6, 165.4, 161.2, 135.4, 132.3, 132.2, 131.5, 129.0 (q, $J_{C-F}$=32.0 Hz), 127.9, 124.1, 123.5 (q, $J_{C-F}$=273.5 Hz), 119.1 (q, $J_{C-F}$=5.5 Hz), 115.1, 67.3; IR (film) cm$^{-1}$ 3347, 3033, 3016, 2988, 2936, 1693, 1575, 1514, 1250, 1163, 768, 678; Mp: 144-145° C.; LRMS (EI): Mass calcd for [M+H]$^+$ C$_{16}$H$_{11}$ClF$_3$NO$_3$: 357.0; found 357.1.

Example 45

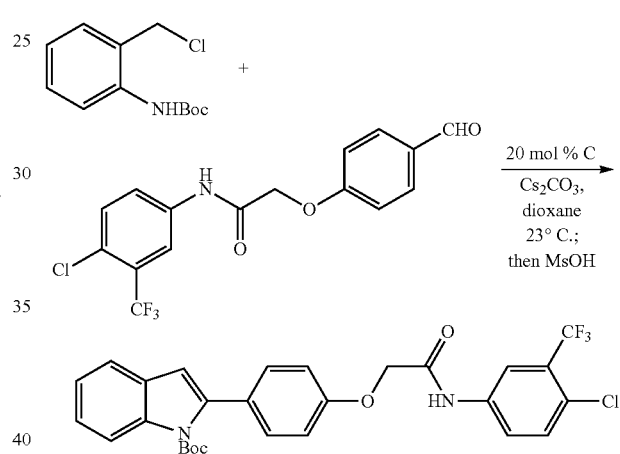

tert-butyl 2-(4-(2-((4-chloro-3-(trifluoromethyl)phenyl)amino)-2-oxoethoxy)phenyl)-1H-indole-1-carboxylate (7). An oven-dried, screw-capped 2 dram vial equipped with a magnetic stirbar was taken into a nitrogen-filled drybox at which time benzyl chloride (79 mg, 0.32 mmol, 1.0 equiv), thiazolium salt C (24 mg, 0.064 mmol, 0.2 equiv), and cesium carbonate (125 mg, 0.38 mmol, 1.2 equiv), and aldehyde 6 (137 mg, 0.384 mmol, 1.2 equiv) were added. The vial was capped with a septum cap, removed from the drybox and put under positive N$_2$ pressure. Into the vial was added 1,4-dioxane (3.2 mL, 0.10 M) via syringe. The reaction was stirred at room temperature until consumption of the benzyl chloride was observed by $^1$H-NMR spectroscopy (38 h). The reaction mixture was opened to the atmosphere and methanesulfonic acid (0.150 mL, 6.5 equiv) was added dropwise with evolution of carbon dioxide. Once the intermediate ketone was consumed (6 min, TLC) the reaction was diluted with dichloromethane (3 mL) and transferred to separatory funnel containing aqueous sodium bicarbonate (1:1 sat. sodium bicarbonate/DI water, 5 mL). The reaction vessel was rinsed with dichloromethane (3×2 mL) and transferred to separatory funnel. After shaking vigorously with venting, the organic phase was separated and the aqueous phase was back extracted with dichloromethane (3×10 mL). The organic phases were combined, washed with brine (15 mL) and the aqueous back extracted with dichloromethane (2×10 mL). The organic portions were combined, dried over anhydrous sodium sulfate, and the solvent was removed in vacuo. Purification by flash chromatography with EtOAc/hexanes/dichloromethane (5%/35%/60%) afforded the title compound 7 (145 mg, 83%) as a clear oil. Analytical data 7: $^1$H NMR (500 MHz, CDCl$_3$) 1H NMR (500 MHz, Chloroform-d) δ 8.39 (s, 1H), 8.15 (d, J=8.3 Hz, 1H), 7.90 (s, 1H), 7.85 (d, J=8.7 Hz, 1H), 7.51 (dd, J=23.0, 8.2 Hz, 2H), 7.41 (d, J=8.4 Hz, 2H), 7.31 (t, J=7.7 Hz, 1H), 7.25 (d, J=5.9 Hz, 1H), 7.02 (d, J=8.4 Hz, 2H), 6.52 (s, 1H), 4.66 (s, 2H), 1.37 (s, 9H); $^{13}$C NMR (CDCl$_3$, 126 MHz) δ 166.3, 156.2, 150.1, 139.5, 137.2, 135.6, 132.1, 130.3, 129.4, 129.1, 128.9 (q, J$_{C-F}$=30.8 Hz), 127.5, 124.3, 123.9, 123.5, 122.9, 120.4, 118.9 (q, J$_{C-F}$=5.4 Hz), 115.2, 114.1, 110.0, 83.5, 67.5, 27.7; IR (film) cm$^{-1}$ 3400, 3119, 3070, 2979, 2931, 2341, 1729, 1703, 1324, 908, 820, 733; LRMS (ESI): Mass calcd for [M+H]$^+$ C$_{28}$H$_{25}$ClF$_3$N$_2$O$_4$: 545.1; found 545.1.

Example 46

Various starting materials and resulting compounds are described herein or can be provided with an amino-protecting group. The term "protecting group," as used herein, is well known in the art and include those described in detail in *Protecting Groups in Organic Synthesis*, T. W. Greene and P. G. M. Wuts, 3rd edition, John Wiley & Sons, 1999, the entirety of which is incorporated herein by reference. Suitable amino-protecting groups include, for instance, methyl carbamate, ethyl carbamate, 9-fluorenylmethyl carbamate (Fmoc), t-butyl carbamate (BOC), benzyl carbamate (Cbz), N-2,5-dimethylpyrrole, p-toluenesulfonamide (Ts) and methanesulfanomide (Ms). Various other protecting groups useful in conjunction with this invention are well-known to those skilled in the art.

Example 47

Starting materials and resulting 2-arylindole compounds are described herein as substituted with various Ar, R$^1$ and R$^2$ moieties. While numerous examples illustrate use of aryl and hetroaryl aldehydes, data provided herein also support use of aliphatic (e.g., without limitation, C$_1$-about C$_8$ alkyl and cycloalkyl) aldehyde starting materials. Likewise, without limitation, R$^1$ and R$^2$ can independently be selected from C$_1$-about C$_6$ alkyl, C$_1$-about C$_6$ alkoxy and C$_1$-about C$_6$ haloalkyl moieties. As would be understood in the art, such moieties are limited only by the commercial or synthetic availability of the corresponding starting material and the present methodology en route to the resulting 2-arylindole compounds.

We claim:

1. A method of preparing a 2-arylindole compound, said method comprising:
providing a reaction medium comprising an N-heterocyclic carbene catalyst precursor compound, a base component and an o-aminobenzyl chloride compound of a formula

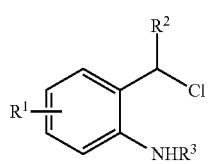

wherein R$^1$ is selected from H, halo, cyano, alkyl, haloalkyl and alkoxy moieties; R$^2$ is selected from H and alkyl moieties; and R$^3$ is selected from H and amino-protecting groups;
introducing an arylaldehyde compound of a formula ArC(O)H to said reaction medium, wherein Ar is selected from aryl and heteroaryl moieties, where a said heteroatom is selected from S and N, said Ar moiety optionally substituted with one or more halo, cyano, alkyl, haloalkyl, alkoxy acetamido or acetamidoalkoxy groups and combinations thereof, to provide a benzylic ketone intermediate compound; and
introducing an acid component to said reaction medium to promote intramolecular N—C bond formation and dehydration, to provide a 2-arylindole compound of a formula

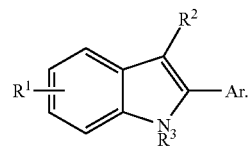

2. The method of claim 1 wherein said base component is a non-nucleophilic carbonate.

3. The method of claim 1 wherein said carbene catalyst precursor compound is selected from azolium and thiazolium compounds.

4. The method of claim 3 wherein said carbene catalyst precursor compound is 3-(2,6-diethylphenyl)-4,5-dimethylthiazol-3-ium perchlorate.

5. The method of claim 4 wherein said base component is cesium carbonate.

6. The method of claim 1 wherein said arylaldehyde is benzaldehyde and provided by benzoin hydrolysis.

7. The method of claim 1 wherein Ar is selected from phenyl, naphthyl, thiophenyl and pyridyl moieties.

8. A method of preparing a 2-arylindole compound, said method comprising:
providing a reaction medium comprising a thiazol-3-ium carbene catalyst precursor compound, a non-nucleophilic base component and an o-aminobenzyl chloride compound of a formula

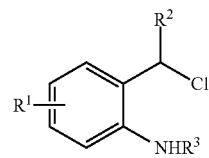

wherein R$^1$ is selected from H, halo, cyano, alkyl, haloalkyl and alkoxy moieties; R$^2$ is selected from H and alkyl moieties; and R$^3$ is selected from H and amino-protecting groups;
introducing 1,4-dioxane and an arylaldehyde compound of a formula ArC(O)H to said reaction medium, wherein Ar is selected from aryl and heteroaryl moieties, where a said heteroatom is selected from S and N, said Ar moiety optionally substituted with one or more halo, cyano, alkyl, haloalkyl, alkoxy, acetamido or acetamidoalkoxy groups and combinations thereof; and introducing an acid component to said reaction medium to promote intramolecular N—C bond formation and dehydration, to provide a 2-arylindole compound of a formula

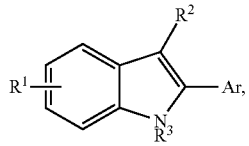

said method in a single reaction vessel absent intermediate isolation and absent transfer of reaction medium.

9. The method of claim 8 wherein said non-nucleophilic base component is a carbonate.

10. The method of claim 8 wherein said carbene catalyst precursor compound is 3-(2,6-diethylphenyl)-4,5-dimethyl-thiazol-3-ium perchlorate.

11. The method of claim 10 wherein said non-nucleophilic base component is cesium carbonate.

12. The method of claim 8 wherein said arylaldehyde is benzaldehyde and provided by benzoin hydrolysis.

13. A method of preparing a 2-arylindole compound, said method comprising:
providing a reaction medium comprising a thiazol-3-ium carbene catalyst precursor compound, a non-nucleophilic base component and an o-aminobenzyl chloride compound of a formula

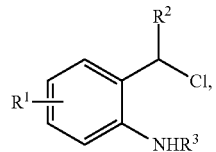

wherein $R^1$ is selected from H, halo, cyano, alkyl, haloalkyl and alkoxy moieties; $R^2$ is selected from H and alkyl moieties; and $R^3$ is selected from H and amino-protecting groups, 1,4-dioxane and an arylaldehyde compound of a formula ArC(O)H, wherein Ar is selected from phenyl, naphthyl, thiophenyl and pyridyl moieties, said Ar moiety optionally substituted with one or more halo, cyano, alkyl, haloalkyl, alkoxy, acetamido or acetamidoalkoxy groups and combinations thereof; and
introducing an acid component to said reaction medium to promote intramolecular N—C bond formation and dehydration, to provide a 2-arylindole compound of a formula

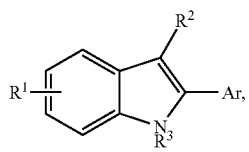

said method in a single reaction vessel absent intermediate isolation and absent transfer of reaction medium.

14. The method of claim 13 wherein said non-nucleophilic base component is a carbonate.

15. The method of claim 13 wherein said carbene catalyst precursor compound is 3-(2,6-diethylphenyl)-4,5-dimethyl-thiazol-3-ium perchlorate.

16. The method of claim 15 wherein said non-nucleophilic base component is cesium carbonate.

17. The method of claim 16 wherein said arylaldehyde is N-(4-chloro-3-(trifluoromethyl)phenyl)-2-(4-formylphenoxyl)acetamide.

18. The method of claim 13 wherein said arylaldehyde is benzaldehyde and provided by benzoin hydrolysis.

19. A method of using an N-heterocyclic carbene catalyst to prepare a 2-arylindole compound, said method comprising:
providing a reaction medium comprising a thiazol-3-ium carbene catalyst precursor compound, a non-nucleophilic base component and an o-aminobenzyl chloride compound of a formula

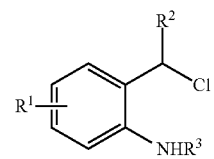

wherein $R^1$ is selected from H, halo, cyano, alkyl, haloalkyl and alkoxy moieties; $R^2$ is selected from H and alkyl moieties; and $R^3$ is selected from H and amino-protecting groups, 1,4-dioxane and an arylaldehyde compound of a formula ArC(O)H, wherein Ar is selected from aryl and heteroaryl moieties, where a said heteroatom is selected from S and N, said Ar moiety optionally substituted with one or more halo, cyano, alkyl, haloalkyl, alkoxy, acetamido or acetamidoalkoxy groups and combinations thereof;
generating an acylanion component from said carbene catalyst precursor compound in said reaction medium; and
introducing an acid component to said reaction medium to promote intramolecular N—C bond formation and dehydration, to provide a 2-arylindole compound of a formula

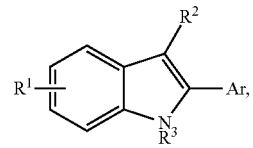

said method in a single reaction vessel absent intermediate isolation and absent transfer of reaction medium.

20. The method of claim 19 wherein said non-nucleophilic base component is a carbonate.

21. The method of claim 19 wherein said carbene catalyst precursor compound is 3-(2,6-diethylphenyl)-4,5-dimethyl-thiazol-3-ium perchlorate.

22. The method of claim 21 wherein said base component is cesium carbonate.

23. The method of claim 22 wherein said arylaldehyde is N-(4-chloro-3-(trifluoromethyl)phenyl)-2-(4-formylphenoxyl)acetamide.

24. The method of claim 19 wherein said arylaldehyde is benzaldehyde and provided by benzoin hydrolysis.

25. A compound of a formula
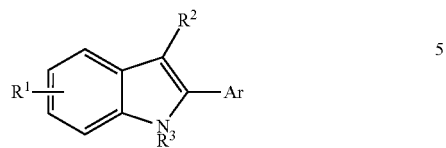
wherein each of $R^1$ and $R^2$ is H, $R^3$ is selected from H and amino-protecting groups and Ar is a 3,4-dibromophenyl moiety.
* * * * *